Figure 1:
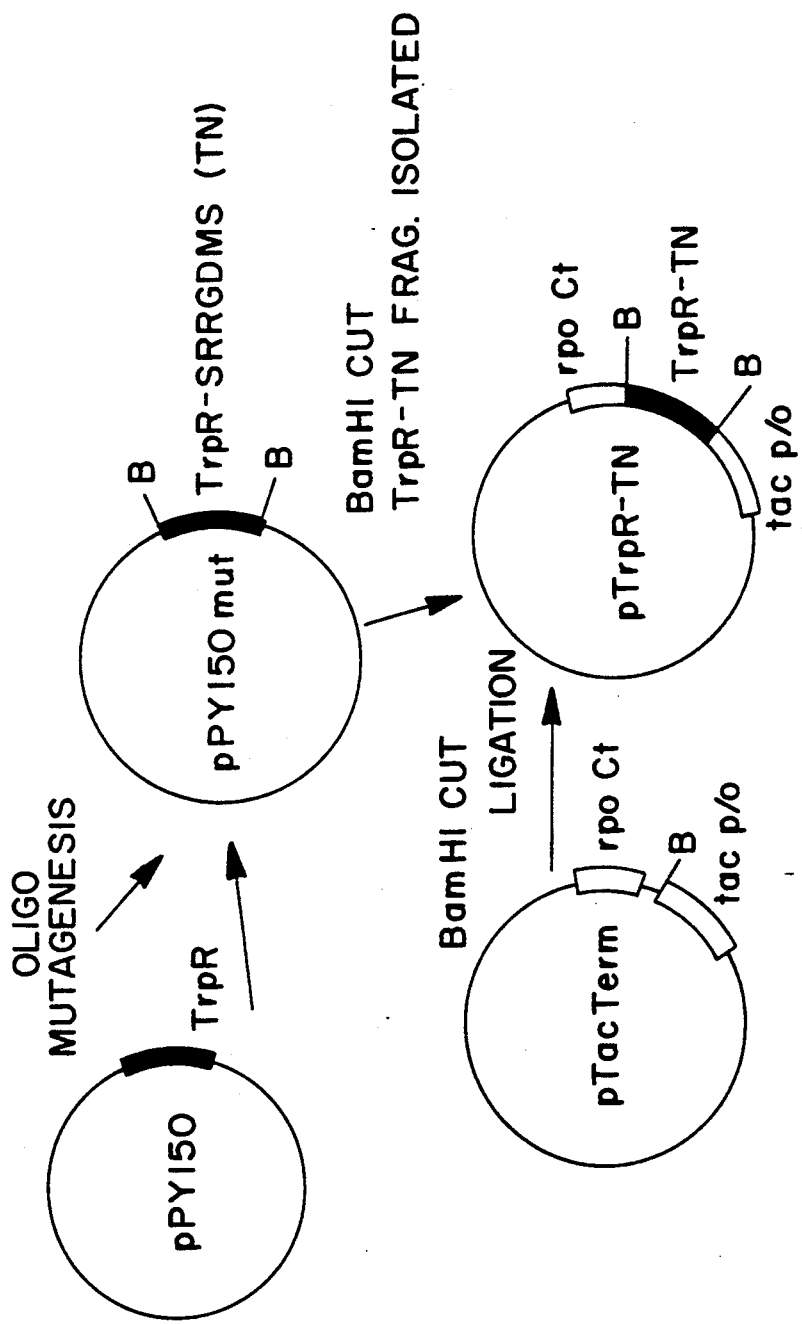

United States Patent [19]

Lernhardt et al.

[11] Patent Number: 5,190,873
[45] Date of Patent: Mar. 2, 1993

[54] HYBRID TRYPTOPHAN APOREPRESSOR CONTAINING LIGAND BINDING SITES

[75] Inventors: Waldemar Lernhardt, Solana Beach; Mario Bourdon, San Diego; Phil Youderian, Ramona, all of Calif.

[73] Assignee: California Institute of Biological Research, La Jolla, Calif.

[21] Appl. No.: 720,222

[22] Filed: Jun. 21, 1991

[51] Int. Cl.$^5$ .................. C07K 13/00; C07K 17/00; C07K 17/02; C12P 21/00
[52] U.S. Cl. .................. 435/177; 435/69.7; 435/69.1; 530/350; 530/812; 930/250
[58] Field of Search .................. 435/91, 69.7, 69.1, 435/177; 530/350, 812; 930/250

[56] References Cited

U.S. PATENT DOCUMENTS 4,703,039  10/1987  Hawiger et al. .................. 514/21

FOREIGN PATENT DOCUMENTS 9100912  1/1991  PCT Int'l Appl. .

OTHER PUBLICATIONS

Botstein, et al. Science 229:1193–1201 1985.
Bass, et al. Science 242:240–245 1988.
Gunsalus, et al. PNAS 77(12) 7117–7121 1980.
Joachimiak et al., *J. Biol. Chem.*, 258:12641–12643 (1983).
Lawson et al., *Nature*, 333:869–871 (1988).
Luisi et al., *Biochim. Biophys. Acta*, 1048:113–126 (1990).
Marmorstein et al., *J. Biol. Chem.*, 262:4922–4927 (1987).
Pfau et al., *Nucl. Acids Res.*, 18:6165 (1990).
Schevitz et al., *Nature*, 317:782–786 (1985).
Arrowsmith et al., *Biochem.*, 29:6332–6341 (1990).
Arvidson et al., *J. Biol. Chem.*, 261:238–243 (1986).
Arvidson et al., *Genetics*, 128:29–35 (1991).
Bourdon et al., *J. Cell Biol.*, 108:1149–1155 (1989).
Joachimiak et al., *Proc. Natl. Acad. Sci. USA*, 80:668–672 (1983).
Zhang et al., *Nature*, 327:591–597 (1987).
Engel et al., *Biochem.* 30: 3161–3169 (1991).

*Primary Examiner*—David L. Lacey
*Assistant Examiner*—Donald E. Adams
*Attorney, Agent, or Firm*—Thomas Fitting

[57] ABSTRACT

Hybrid proteins containing repressor proteins and substituted receptor binding sites, amino acid and DNA sequences encoding the hybrid proteins are provided. Methods for preparing the hybrid proteins are also described.

19 Claims, 6 Drawing Sheets

HYBRID TRYPTOPHAN APOREPRESSOR CONTAINING LIGAND BINDING SITES

This invention was made with government support under government contract 5 29 CA45506 awarded by the National Institutes of Health. The government has certain rights in the invention.

FIELD OF THE INVENTION

This invention relates to hybrid proteins constructed from prokaryotic repressor proteins and receptor binding sites, and to the methods for producing the hybrid proteins.

BACKGROUND OF THE INVENTION

Receptors are molecules, typically proteins or glycoproteins, found on the surface of cells, including mammalian cells, that possess specific affinity for other molecules known as ligands. Ligands may be small or large (macro) molecules such as proteins. Binding of ligands to receptors on the surface of mammalian cells elicits dramatic responses or "signals" in the cells such as proliferation and adhesion. These cellular responses involve protein-protein interactions and intercellular interactions that regulate important physiological processes, such as the humoral immune response. Defects in receptor structure and function may interfere with recognition of ligands by the cell-bound receptors resulting in disease or dysfunction and death.

Many cell surface receptors and their corresponding ligands have been identified and characterized structurally and biochemically. The study of protein-mediated intercellular signalling yields the surprising result that only short stretches of amino acids, e.g. at least three amino acids, on the surfaces of mammalian proteins are both necessary and sufficient to bind specific receptors and thereby elicit dramatic cellular responses.

Examples of characterized receptors include complement receptor type 2 (CD21 or "CR2") (Weigle et al., In Complement, Muller-Eberhard and Miescher, Eds., Springer-Verlag, Berlin, p. 323 (1985)). The clonal expansion of mature, antigen-reactive B lymphocytes in the humoral immune response is regulated both by direct intercellular interactions (with T helper lymphocytes and accessory cells), and by interactions with soluble growth factors (Unanue, *Adv. Immunol.*, 15:95 (1972)). These soluble factors include B cell growth factors, interleukins, interferons, and components of the complement system (O'Garra et al., *Immunol. Today*, 8:45 (1988); Weigle et al., supra). Members of the latter two classes of proteins bind specific cell surface receptors, including CR2. CR2 is the B lymphocyte receptor for the proteolytic activation products C3bi, C3dg and C3d of complement component C3 (Cooper et al., *Ann. Rev. Immunol.*, 6:85 (1988); Aggregated C3b and C3d induce B cell proliferation (Erdei et al., *Eur. J. Immunol.*, 15:184 (1985); Melchers et al., *Nature*, 317:264 (1985)). CR2 is also the receptor for Epstein-Barr virus (EBV), a potent polyclonal B cell activator (Fingeroth et al., *Proc. Natl. Acad. Sci. USA*, 81:4510 (1985); Frade et al., *Proc. Natl. Acad. Sci. USA*, 82:1490 (1985)). CR2 plays a central role in signalling B cell proliferation (Cooper et al., supra (1988)). Several monoclonal antibodies and polyclonal anti-CR2 antisera stimulate T cell-dependent B cell proliferation (Cooper et al., supra (1988)). Furthermore, ligand binding to CR2 is necessary for the transition from $G_1$ to S phase of the B cell cycle of human and murine preactivated blasts (Melchers, supra (1985); Bohnsack and Cooper *J. Immunol.*, 141:2569 (1988)). CR2 is also phosphorylated during B cell stimulation, a common property of growth factor receptors (Changelian and Fearon *J. Exp. Med.*, 161:101 (1986)).

CR2 occurs on normal and malignant B lymphocytes (Cooper et al., supra (1988); Hatzfeld et al , *J. Immunol.*, 140:170 (1988)), on epithelial cells (Young et al., *The Lancet*, 240 (1986)), and, to a lesser extent, on immature thymocytes and follicular dendritic cells (Tsoukas and Lambris, *Eru. J. Immunol.*, 18:1299 (1988); Reynes et al., *J. Immunol.*, 135:2687 (1985)). The primary structure of CR2 has been deduced from the DNA sequence of its clone. Human CR2 is a membrane glycoprotein of 145 kd, and has sequence similarity to other members of the family of complement binding proteins.

The recognition sites on CR2 for C3d and EBV have been located on the N-terminal part of this longitudinal molecule. The sequence motifs on C3 and EBV coat protein, gp350, that mediate binding to CR2 receptor have also been defined (Lambris et al., *Proc. Natl. Acad. Sci. USA*, 82:4235 (1985); Nemerow et al., *Cell* 56:369 (1989)) (Table 1). Synthetic hexapeptides with the sequence of the CR2 binding site on C3 inhibit human and murine B cell proliferation (Lernhardt et al., *Immunol. Rev.*, 99:239 (1987)). Thus CR2 receptor can bind both monomeric C3d and aggregated C3d as ligands, as well as the major epitope of EBV capsid protein.

CR2 ligands act in concert with other B cell growth modulators, including growth factors, lymphokines, and cytokines. Thus, the growth-inducing effect of anti-CR2 monoclonal antibody OKB7 is T cell-dependent, and requires T cell-derived B cell growth factors (Cooper et al., supra (1988)). It has been shown that optimal cell cycle progression and cell division occurs only in the presence of both anti-Ig antibodies and IL-2 or IL-5.

The CR2 receptor is of clinical interest, because it is the receptor for Epstein-Barr virus (EBV) (Frade supra (1985)). EBV is the causative agent of infectious mononucleosis (Huang et al., *Int. J. Cancer* 14:580 (1974)), and possibly is a human cancer virus, because its presence is correlated with nasopharyngeal carcinoma and Burkitt's lymphoma (Henle et al., *Science*, 157:1064 (1967)). In addition, EBV may play a role in the onset of B cell neoplasia observed in a substantial fraction of AIDS patients (Yarchoan et al., *J. Clin. Invest.*, 78:439 (1986)). At the least, a substantial fraction of AIDS patients have chronic EBV infections. Exposure of pregnant women to individuals infected with and shedding EBV poses a significant risk to fetal development. It would be useful to better understand the mechanism of CR2 ligand action and to design and engineer proteins that function as recombinant inhibitors of EBV infection and lymphoma proliferation.

Prokaryotic repressors are small, multimeric proteins that are easy to manipulate genetically. Prokaryotic repressors bind short stretches of DNA called operators. Aporepressor proteins bind operators poorly and must complex with other small molecules called corepressors, such as tryptophan or S-adenosylmethionine to form active repressor complexes, or simply, repressors. Corepressors act as "keystones" that fit into and stabilize the hydrophobic cores of their aporepressors.

The *E. Coli* Tryptophan (Trp) aporepressor monomer is a peptide 108 amino acids long ($M_r = 12,356$ daltons) (Gunsalus and Yanofsky, *Proc. Nat. Acad. Sci.*

USA, 77:7117–7121 (1980)) that assembles as a dimer (Joachimiak et al., *Proc. Natl. Acad. Sci. USA*, 80:668–672 (1983); Arvidson et al., *J. Biol. Chem.*, 261:238–243 (1986)). Trp aporepressor binds DNA poorly in the absence of the corepressor ligand, L-tryptophan (or the analog 5-methyltryptophan, 5-MT). Aporepressor assembles with tryptophan or 5-MT to form active Trp repressor complex, a global repressor that binds operator sites to regulate the initiation of transcription from at least three different *E. coli* promoters. In addition, aporepressor can form inactive Trp pseudorepressor complexes with indole-3-propionic acid (IPA) or indole-π-acrylic acid (IAA); these pseudo-repressor complexes bind operator DNA more poorly than aporepressor (Doolittle and Yanofsky, *J. Bacteriol.*, 95:1283–1294 (1968); Baker and Yanofsky, *Proc. Natl. Acad. Sci USA*, 60:313–320 (1968)).

Trp aporepressor controls three operons that comprise a system to maintain the concentration of L-tryptophan in *E. coli* homeostatically, within levels necessary for efficient protein synthesis. When concentrations of intracellular tryptophan are low, TrpR exists predominantly as an aporepressor that cannot bind trp operator DNA, and the trpEDCBA biosynthetic genes are expressed maximally. When L-tryptophan levels are high, a substantial fraction of TrpR is active repressor, and tryptophan biosynthesis slows (Cohen and Jacob, *C.R. Acad. Sci. Paris*, 248:3490–3492 (1959); Yanofsky, *J. Amer. Med. Assoc.*, 218:1026–1035 (1971); Bennet et al., *Proc. Natl. Acad. Sci. USA*, 73:2351–2355 (1976); Zurawski et al., *J. Mol. Biol.*, 145:47–73 (1981); Yanofsky et al., *J. Bacteriol.*, 158: 1018–1024 (1984)). Trp aporepressor regulates a biosynthetic pathway in response to the amount of an end product; thus, it functions as a rheostat, rather than an on/off switch. In contrast, μ and other phage repressors control binary developmental decisions, and are not known to respond to small ligands. Other ligand-activated DNA-binding proteins have been studied to lesser extents.

The X-ray crystal structures of two forms of Trp repressor (Schevitz et al., *Nature*, 317:782–786 (1985); Lawson et al., *Proteins*, 3:18–31 (1988)), aporepressor (Zhang et al., *Nature*, 327:591–597 (1987)), and pseudorepressor (Lawson et al., *Nature*, 333:869–871 (1988)) have been determined, and show that, when crystallized, the peptide monomer is a bundle of six α-helices with a disordered, 11-residue N-terminal arm. The TrpR dimer has a remarkable subunit interface, in which four of each subunit's six α-interface, helices (A, B, C, and F) are interlocked. The amino acid sequence of the two flexible α-helices, D and E, resembles the conserved "helix-turn-helix" DNA-binding motif characteristic of many prokaryotic repressors, and pairs of the 2° substructures formed by the D loop and E are positioned on the surface of Trp repressor to contact successive major grooves of trp operator DNA. Genetic analyses of mutant TrpR genes show that residues from both D and E are critical for DNA-binding (Bass et al., *Science*, 242:240–245 (1988); Kelly et al., *Proc. Natl. Acad. Sci USA*, 79:3120–3124 (1982)).

Recently, Arrowsmith, Jardetsky and coworkers have determined the structure of Trp repressor in solution, using $^1$H-NMR spectroscopic methods (Arrowsmith et al., *Biochemistry*, 29:6332 (1990); Arrowsmith and Jardetsky, submitted for publication (1991). Their results show that the structure of Trp repressor in solution resembles the crystal structures closely, with two major differences. In solution, the first half of A is partially disordered, and the residues organized as D in the crystal do not form an α-helix, but rather comprise some sort of surface loop (the "D Loop") (Arrowsmith et al., supra (1990)). The binding of the corepressor, L-tryptophan, restricts the motion of the D loop; amide protons of residues in D become less solvent-accessible in the presence of corepressor. However, corepressor binding does not elicit a coil-to-helix transition, because these protons remain uninvolved in H-bond formation in the repressor complex and in the specific repressor/operator complex [Arrowsmith and Jardetsky, supra.

Trp aporepressor is usually stable, and may be purified in large quantities (Arvidson et al., In Protein Purification: Micro to Macro, UCLA Symp. Mol. Cell Biol (Ed. Burgess), Alan R. Liss, NY; (1986); Smith et al., *Proc. Natl. Acad. Sci., USA*. 82:6104–6108 (1985)). In addition, to understand how particular amino acids contribute to the structure and function of Trp repressor, methods have been developed for both mismatch-primer (Arvidson et al., *Genetics*, 128 (1991) and cassette-style (Pfau and Youderian, *Nuc. Acids Res.*, 18:6165 (1990) mutagenesis of either single or multiple adjacent codons of TroR. Mutagenesis may be coupled with a rapid screen for Trp repressor function; this screen depends on the color of colonies made by a strain of bacteria, CG103, which overproduces Trp repressor.

Comparisons of the NMR structures of Trp aporepressor and repressor suggests that the binding of indole analogs results in subtle changes in the orientation of D and E relative to the stationary hydrophobic core of the protein. The TrpR dimer has two identical, independent binding sites for corepressor (Arvidson et al., supra (1986); Marmorstein et al., *J. Biol. Chem.*, 262:4922–4927 (1987)); surprisingly, these are formed by the side chains of residues from both monomers in a dimer (Schevitz et al., supra (1985)). The interactions that each corepressor is predicted to make with aporepressor are primarily hydrophobic. Presumably, the binding of corepressor restricts the ensemble of preferred conformations of the DNA-binding domains of an aporepressor to a subset of conformations that bind DNA with lower free energies (pseudorepressor binding restricts aporepressor conformations to a subset that binds DNA with higher free energies).

Attempts have been made to construct hybrids between structural proteins and receptor binding sites. For example, hybrids between proteins having highly repetitive sequences such as silk-like protein (SLP) and the ten-residue RGD motif of fibronectin have been described (Cappello and Crissman, *Chemical and Engineering News*, pp. 26–32 (July 16, 1990)). Although the hybrid protein is active in vitro, its highly repetitive gene is unstable.

It would be advantageous to provide a method for producing hybrid proteins containing receptor binding sites, that are active as ligands for mammalian cell receptors to design reagents for a variety of applications including treatment of diseases resulting from receptor/ligand dysfunction.

SUMMARY OF THE INVENTION

The present invention provides such method and hybrid proteins. The hybrid proteins are produced from a prokaryotic repressor protein and a peptide segment that is heterologous to (not naturally present in) the repressor. Preferably, the peptide segment defines a binding site from a ligand reactive with a mammalian cell surface receptor. Examples of prokaryotic repressor protein that may be used include TrpR aporepressor protein, MET aporepressor protein, bacteriophage lambda, Lac repressor, bacteriophage P22 Arc repressor and the like. The invention also provides DNA sequences encoding the amino acid sequences of the invention, vectors containing the DNA sequence and host cells transfected with the vectors.

The receptor binding site can be obtained from interferon alpha, fibrinogen gamma, tenascin, fibronectin, and the like. Viral immunogenic pathogen derived proteins, such as proteins from HIV, EBV, hepatitis B and the like can also be used.

The invention also provides a method for preparing a hybrid protein prokaryotic repressor protein containing at least one substituted binding site from a ligand reactive with an eukaryotic cell surface receptor by 1) mutating the DNA codons for at least one selected amino acid in the amino acid sequence encoding the prokaryotic repressor to encode a contiguous sequence of amino acids that encodes a selected receptor binding site from a ligand reactive with an eukaryotic cell receptor to produce a mutated amino acid sequence; 2 a hybrid protein encoded by the mutated DNA sequence that has the activity of the selected receptor binding site; and isolating the hybrid protein produced. The hybrid protein is then purified and tested for biological activity as a binding site for eukaryotic cell receptors. The hybrid protein is produced by recombinant means or by chemical synthesis. A preferred prokaryotic repressor protein is Trp aporepressor.

BRIEF DESCRIPTION OF THE DRAWINGS

FIG. 1 is a diagram illustrating the Construction of pTrpR-TN Plasmids. Single stranded DNA template was prepared by M13 infection of CJ236 transformed with pPY150. Site direct mutagenesis was done on single stranded DNA with oligonucleotides (38–45 mer) and transformation into CG103F.Kan. Tac P/O tac promotor/operator fragment rpoc+: rpoC transcription terminator.

FIG. 2 illustrates cell Attachment to TrpR-TN5. Shown is cell attachment (relative fluorescence) of Di-I stained U251 human glioma cells to wells elated with increasing amounts of TrpR-TN5 as described in Example 7.

FIG. 3 illustrates cell Attachment to TrpR-TN5 and TrpR-TN1. Shown is cell attachment of U251 cells to TrpR-TN5, TrpRTN1 and TrpR in the presence (+) or absence 6(−) of 1mg/ml SRRGDMS peptide as described in Example 7.

FIG. 4 illustrates peptide Inhibition of Cell Attachment to Trp-TN5. Increasing concentrations of peptide SRRGDMS-$NH_2$ and GRGDSP-$NH_2$ were present in cell attachment assays on TrpR-TN5 as described in Example 7. The control peptide MGSRSRD did not inhibit cell attachment.

FIG. 5 illustrates $\alpha_v\beta_3$-liposome binding to TrpR-TN5. Receptor liposomes were prepared by dialyses of receptor and phosphatidylcholine (PC) plus $^3$H-PC as described in Example 7. Shown is liposome binding to fibronectin (FN) vitronectin (VN), TrpR-TN5, and TrpR coated wells.

FIG. 6 illustrates inhibition of Cell Attachment by LM609 Anti $\alpha_v\beta_3$. Shown is cell attachment in media (or monoclonal antibody 81C6 1/200) and in presence of LM 609 1/200 as described in Example 7.

DETAILED DESCRIPTION OF THE INVENTION

DEFINITIONS

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 C.F.R. 1.822(b)(2)), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| J | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified an unusual amino acids, such as those listed in 37 C.F. R. 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Nucleotide: A monomeric unit of DNA or RNA consisting of a sugar moiety (pentose), a phosphate, and a nitrogenous heterocyclic base. The base is linked to the sugar moiety via the glycosidic carbon (1′ carbon of the pentose) and that combination of base and sugar is a nucleoside. When the nucleoside contains a phosphate group bonded to the 3′ or 5′ position of the pentose it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus.

Base Pair (bp): A partnership of adenine (A) with thymine (T), or of cytosine (C) with guanine (G) in a double stranded DNA molecule. In RNA, uracil (U) is substituted for thymine.

Nucleic Acid: A polymer of nucleotides, either single or double stranded.

Polynucleotide: a polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, probes, RNA/DNA segments, oligonucleotides or "oligos" (relatively short polynucleotides), genes, vectors, plasmids, and the like.

Gene: A nucleic acid whose nucleotide sequence codes for an RNA or polypeptide. A gene can be either RNA or DNA.

Duplex DNA: a double-stranded nucleic acid molecule comprising two strands of substantially complementary polynucleotides held together by one or more hydrogen bonds between each of the complementary bases present in a base pair of the duplex. Because the nucleotides that form a base pair can be either a ribonucleotide base or a deoxyribonucleotide base, the phrase "duplex DNA" refers to either a DNA-DNA duplex comprising two DNA strands (ds DNA), or an RNA-DNA duplex comprising one DNA and one RNA strand.

Complementary Bases: Nucleotides that normally pair up when DNA or RNA adopts a double stranded configuration.

Complementary Nucleotide Sequence: A sequence of nucleotides in a single-stranded molecule of DNA or RNA that is sufficiently complementary to that on another single strand to specifically hybridize to it with consequent hydrogen bonding.

Conserved: A nucleotide sequence is conserved with respect to a preselected (reference) sequence if it nonrandomly hybridizes to an exact complement of the preselected sequence.

Hybridization: The pairing of substantially complementary nucleotide sequences (strands of nucleic acid) to form a duplex or heteroduplex by the establishment of hydrogen bonds between complementary base pairs. It is a specific, i.e. non-random, interaction between two complementary polynucleotides that ca be competitively inhibited.

Nucleotide Analog: A purine or pyrimidine nucleotide that differs structurally from A, T, G, C, or U, but is sufficiently similar to substitute for the normal nucleotide in a nucleic acid molecule.

DNA Homolog: Is a nucleic acid having a preselected conserved nucleotide sequence and a sequence coding for a receptor capable of binding a preselected ligand.

Recombinant DNA (rDNA) molecule: a DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

Vector: a rDNA molecule capable of autonomous replication in a cell and to which a DNA segment, e.g., gene or polynucleotide, can be operatively linked so as to bring about replication of the attached segment. Vectors capable of directing the expression of genes encoding for one or more proteins are referred to herein as "expression vectors". Particularly important vectors allow cloning of cDNA (complementary DNA) from mRNAs produced using reverse transcriptase.

Receptor: A receptor is a molecule, such as a protein, glycoprotein and the like, that can specifically (non-randomly) bind to another molecule.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Monoclonal Antibody: The phrase monoclonal antibody in its various grammatical forms refers to a population of antibody molecules that contains only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen, e.g., a bispecific monoclonal antibody.

Fusion Protein: A protein comprised of at least two polypeptides and a linking sequence to operatively link the two polypeptides into one continuous polypeptide. The two polypeptides linked in a fusion protein are typically derived from two independent sources, and therefore a fusion protein comprises two linked polypeptides not normally found linked in nature.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Cistron: Sequence of nucleotides in a DNA molecule coding for an amino acid residue sequence and including upstream and downstream DNA expression control elements.

Stop Codon: Any of three codons that do not code for an amino acid, but instead cause termination of protein synthesis. They are UAG, UAA and UGA and are also referred to as a nonsense or termination codon.

The present invention concerns a method for preparing hybrid proteins consisting of prokaryotic repressors and receptor binding sites.

In the method of the invention, surface features of a stable, prokaryotic repressor, such as Trp aporepressor, are replaced with short peptide segments (oligopeptides) that are active as ligand binding sites for receptors produced by eukaryotic cells, such as antibodies, T-cell receptor, hormone receptors, and the like. The prokaryotic repressor acts as a scaffold, or "context" protein, for presentation of the peptide segment.

The peptide segment is typically at least 3, and preferably at least 5, and usually no more than about 20, and preferably no more than about 10, amino acid residues in length. Usually, the peptide segment will be in the range of 6 to 9 (inclusive) residues in length. The length must be sufficient for the segment to form a binding site such that the hybrid protein mimics at least one biological activity, as evidenced by binding, of the native protein ligand from which it is derived.

An exemplary hybrid protein is a tryptophan aporepressor containing within its amino acid residue sequence a peptide segment that is heterologous to (not naturally occurring within) the aporepressor. The peptide segment is located within the amino acid residue sequence of the hybrid protein such that it is expressed on the protein's solvent-accessible surface. Typically, the peptide sequence is flanked by amino-terminal and carboxy-terminal sequences corresponding to respective amino-and carboxy-terminal sequences of the aporepressor protein. However, the peptide segment can also be located at the amino- or carboxyterminus of the hybrid protein.

When the peptide segment is inserted or substituted between two flanking sequences, the amino acid residue sequence of the hybrid protein can be represented by the formula, read from left to right and in the direction of amino-terminus to carboxyterminus:

Z—B—U,

In the formula, Z is an amino-terminal portion of the tryptophan aporepressor, and U is a carboxyterminal portion of the tryptophan aporepressor. The lengths of Z and U are selected (adapted) such that B, the peptide segment, is expressed on the surface of the hybrid protein. Factors considered when adapting the length of Z and U are the length in residues of B, whether B is substituted or inserted without substitution into the aporepressor's native sequence, and in view of forming hybrid protein whose overall amino acid residue sequence length is about 100 to about 120 residues, preferably about 105 to about 115 residues, and more preferably about 108 to 112 residues. Typically, when the *E. coli* tryptophan aporepressor is used as the context protein, the hybrid protein length will be in the range of 108 residues because that is the length of the native aporepressor. For example, when a peptide segment that is 15 residues in length is to be inserted between flanking portions of the *E.coli* tryptophan aporepressor protein, about 15 residues should be deleted from the native aporepressor sequence to a hybrid protein length equivalent to that of the native aporepressor, i.e. about 108 residues. The residues to be deleted are those adjacent to the insertion site, i.e. interior residues, while the terminal portions, i.e. the amino- and carboxy- most (terminal) residues, are left intact. The dashes in the formula represent peptide bonds that link the flanking sequences to the peptide segment. Preferred hybrid proteins are represented by the amino acid residue sequences SEQ ID NO 1 through SEQ ID NO 19 listed below.

| SEQ ID NO | |
|---|---|
| (1) | MAQQ-B-<br>AAMAEQRHQEWLRFVDLLKNAYQNDLHLPLLNLMLTPDEREALGT<br>RVRIVEELLRGEMSQRELKNELGAGIATITRGSNSLKAAPVELRQW<br>LEEVLLKSD |
| (2) | MAQQSPYSAAMAEQRHQEWLRFVDLLKNAYQNDLHLPLLNLMLTPD<br>EREALGTRVRIVEE-B-<br>SQRELKNELGAGIATITRGSNSLKAAPVELRQWLEEVLLK SD |
| (3) | MAQQSPYSAAMAEQRHQEWLRFVDLLKNAYQNDLHLPLLNLMLTPD<br>EREALGTRVRIVEELLRGEM-B-<br>ELGAGIATITRGSNSLKAAPVELRQWLEEVLLKSD |
| (4) | MAQQSPYSAAMAEQRHQEWLRFVDLLKNAYQNDLHLPLLNLMLTPD<br>EREALGTRVRIVEELLRGEMSQRELK-B-<br>ATITRGSNSLKAAPVELRQWLEEVLLKSD |
| (5) | MAQQSPYSAAMAEQRHQEWLRFVDLLKNAYQNDLHLPLLNLMLTPD<br>EREALGTRVRIVEELLRGEMSQRELKN-B-<br>ITRGSNSLKAAPVELRQWLEEVLLKSD |
| (6) | MAQQSPYSAAMAEQRHQEWLRFVDLLKNAYQNDLHLPLLNLMLTPD<br>EREALGTRVRIVEELLRGEMSQRELKNELGAGIATITRGSNSLKAA<br>PVELRQWLEEVLLKSD-B |
| (7) | MAQQSPYSAAMAEQRHQEWLRFVDLLKNAYQN-B-<br>LHLPLLNLMLTPDEREA<br>LGTRVRIVEELLRGEMSQRELKNELGAGIATITRGSNSLKAAPVEL<br>RQWLEEVLLKSD |
| (8) | MAQQ-B-<br>SPYSAAMAEQRHQEWLRFVDLLKNAYQNDLHLPLLNLMLTPDERE<br>ALGTRVRIVEELLRGEMSQRELKNELGAGIATITRGSNSLKAAPVE<br>LRQWLEEVLLKSD |
| (9) | MAQQSPYSAAMAEQRHQEWLRFVDLLKNAYQ-B-<br>LHLPLLNLMLTPDEREAL<br>GTRVRIVEELLRGEMSQRELKNELGAGIATITRGSNSLKAAPVELR<br>QWLEEVLLKSD |
| (10) | MAQQSPYSAAMAEQRHQEWLRFVDLLKNAYQNDLHLPLLNLMLTPD<br>EREALGTRVRIVEELL-B-<br>QRELKNELGAGIATITRGSNSLKAAPVELRQWLEEVLLK SD |
| (11) | MAQQSPYSAAMAEQRHQEWLRFVDLLKNAYQNDLHLPLLNLMLTPD<br>EREALGTRVRIVEELLRGEMSQ-B- |

-continued

| SEQ ID NO | |
|---|---|
| | GIATITRGSNSLKAAPVELRQWLEEVLLKSD |
| (12) | MAQQSPYSAAMAEQRHQEWLRFVDLLKNAYQNDLHLPLLNLMLTPD<br>EREALGTRVRIVEELLRGEMSQRE-B-<br>ATITRGSNSLKAAPVELRQWLEEVLLKSD |
| (13) | MAQQSPYSAAMAEQRHQEWLRFVDLLKNAYQNDLHLPLLNLMLTPD<br>EREALGTRVRIVEELLRGEMSQRELKNELGAGIATITRGSNSLKAA<br>PVELRQWLEEVLL-B- |
| (14) | MAQQSPYSAAMAEQRHQEWLRFVDLLKNAYQNDLH LPLLNLML-B-<br>TRVRI<br>VEELLRGEMSQRELKNELGAGIATITRGSNSLKAAPVELRQWLEEV<br>LLKSD |
| (15) | MAQQSPYSAAMAEQRHQEWLRFVDLLKNAYQNDLHLPLLNLMLTPD<br>EREALGTRVRIVEELLRGEMSQR-B-<br>IATITRGSNSLKAAPVELRQWLEEVLLKSD |
| (16) | MAQQS-B-<br>AAMAEQRHQEWLRFVDLLKNAYQNDLHLPLLNLMLTPDEREALGTR<br>VRIVEELLRGEMSQRELKNELGAGIATITRGSNSLKAAPVELRQWL<br>EEVLLKSD |
| (17) | MAQQSPYSAAMAEQRHQEWLRFVDLLKNAYQNDLHLPLLNLMLTPD<br>EREALGTRVRIVEEL-B-<br>QRELKNELGAGIATITRGSNSLKAAPVELRQWLEEVLLK SD |
| (18) | MAQQSPYSAAMAEQRHQEWLRFVDLLKNAYQNDLHLPLLNLMLTPD<br>EREALGTRVRIVEELLRGEMS-B-<br>ELGAGIATITRGSNSLKAAPVELRQWLEEVLLK SD |
| (19) | MAQQSPYSAAMAEQRHQEWLRFVDLLKNAYQNDLHLPLLNLMLTPD<br>EREALGTRVRIVEELLRGEMSQRELKN-B-<br>ATITRGSNSLKAAPVELRQWLEEVLLK SD |

When the peptide segment is located at the amino- or carboxy-terminus of the hybrid protein, the hybrid protein is represented by the formula B-U or Z-B, respectively, where Z and U are carboxy- or amino-terminal aporepressor sequences as previously described, and B is the peptide segment.

The phrases "surface accessible" and "surface expression" indicate that the peptide segment is positioned within the primary structure of the hybrid protein so that it is available for specific binding by a receptor when the hybrid is in a physiologically tolerable aqueous solution. Windows or zones which are available for surface expression or which are surface accessible in the *E. coli* tryptophan aporepressor are defined by residues 5–, 44–52, 61–67, 67–77, 71–81 and 108 of the native protein sequence as shown in SEQ ID NO 20.

In one embodiment of the invention, binding sites on the proteins interferon alpha (IFN) and gp350 (EBV coat protein) that interact with one major eukaryotic B lymphocyte surface receptor, CR2, are substituted or inserted as peptide segments into the *E. coli* Trp aporepressor protein to form novel hybrid proteins.

In another embodiment, the hybrid proteins, at the DNA level, are substrates for subsequent site-directed mutagenesis to generate mutant binding sites with altered biological properties, e.g. greater affinity for receptor, to provide additional hybrid proteins with novel activities.

Peptide segments forming binding sites can be substituted for or inserted into regions of the aporepressor regions whose conformation is restricted by corepressor binding, without disturbing the corepressor binding pocket. Corepressor analogs may be used to modify the conformations of the peptide segments. Thus, several different conformations of each peptide segment in the hybrid Trp aporepressor may be made with different resulting activities.

The method of the invention for preparing hybrid proteins is carried out as follows. Mutagenesis is performed on single or multiple codons of the prokaryotic repressor gene using a procedure such as that described by Kunkel (*Proc. Natl. Acad. Sci. USA* 82:488–492 (1985)) and, typically, an additional restriction selection step as described Wells, *Philos. Trans. R. Soc. Lond.* Ser. A 317:415–423 (1986)). In this procedure, the gene encoding the prokaryotic repressor, for example Trp aporepressor, is prepared, for example by introducing unique restriction endonuclease sites, and is inserted into an appropriate plasmid, such as pPY150, a rop$^{+}$- derivative of pBR322, which expresses trpR from the lacUV5 promoter (Bass, *Science* 242:240–245 (1988)) or pTACTERM, a rop pBR322 derivative and site-directed mutagenesis to alter the sequence of the repressor to encode a desired peptide segment receptor binding site). This method can be used to make single changes, or to "randomize" a codon by replacing it with the mixed sequence NNS, in which N can be any of the four DNA nucleotides A, C, G or T and S can be C or G. This sequence represents all 20 amino acids with 32 codons.

Substitutions are made in the prokaryotic repressor using site-directed mutagenesis as described above to alter the DNA sequence to replace a stretch of contiguous DNA in the sequence of the repressor with the sequence of at least one selected binding site. Preferably, the selected binding site substituted into the prokaryotic repressor comprises at least three, and preferably five amino acids. The gene encoding the repressor and substituted receptor binding site is then cloned and expressed using standard molecular biology procedures. The hybrid protein products are then purified to provide a hybrid repressor protein containing the substituted receptor binding site or sites.

Activity of the resulting hybrid protein is confirmed using a binding assay appropriate for the ligand being mimicked. Typically, this involves determining whether the protein binds t cells containing the receptor reactive with the binding site. Hybrid Trp repressor protein containing the tenascin receptor binding site Bourdon et al., *J. Cell. Biol.,* 108:1149–1155 (1989) as described in Example 7, infra, an assay to determine whether the hybrid protein binds to human tumor cells is carried out using the all attachment assay described by Bourdon et al., supra.

The present invention also contemplates performing further mutagenesis in the receptor binding site sequences after prior mutagenesis of the repressor protein to provide the binding site sequence in the repressor protein to identify hybrid proteins with desired activities. Changes are made in the flanking codons for amino acid residues of the binding site in the hybrid protein to optimize the presentation of the site to its corresponding receptor. In addition, single amino acid changes are made in the binding site to optimize the primary sequence of the site. These will include mutations that increase the specific activity of the site as determined by standard binding assays.

Hybrid proteins produced by the methods of the invention may be used as reagents for treatment of or introduction into humans to combat infection or disease caused by defects in the interaction of the receptor and its ligands. Thus, binding sites for receptors from proteins involved in infection, for example from EBV virus proteins, may be engineered in hybrid proteins using the methods of the invention to combat EBV infection. Such proteins may mimic a compound such as interferon in vivo to block the binding or subsequent interactions of ligands to or with the receptors for EBV, preventing the effects of infection by this virus.

Therapeutic applications of the hybrid proteins of the invention are carried out using pharmaceutical compositions containing a pharmaceutically effective amount of the hybrid protein and a pharmaceutically acceptable carrier. The compositions may additionally include other reagents for treatment. Such compositions are administered using conventional modes of administration including, but not limited to, topical, intravenous, intraperitoneal, oral and intralymphatic introduction. The hybrid proteins are used in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The compositions containing the hybrid proteins of the invention also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the compositions of the invention depends on the severity and course of the disease or dysfunctions, the patient's health and response to treatment, and the judgment of the treating physician. Accordingly, the dosages of the compositions are titrated to the individual patient.

Quantities of the hybrid proteins of the invention may be readily made and purified using additional standard procedures such as immunoaffinity, gel exclusion chromatography, ion exchange chromatography electrophoresis, and the like. Purified hybrid proteins may be used as vaccines to immunize against certain disease. Procedures for preparing such vaccines are known in the art (see, e.g. Estin et al., *Proc. Natl. Acad. Sci.* (USA) 85:1052 (1988)). Briefly, recombinant viruses are constructed for expression of the cloned gene encoding the hybrid protein. Cells infected with the recombinant viruses will express the hybrid protein at the surface of the cells together with the host's incompatibility antigens and immunogenic viral proteins. This favors the induction of cellular immunity which plays a key role in tumor rejection. A suitable virus, for example vaccinia virus derived from a plaque-purified virus of the Wyeth smallpox vaccine (New York City Board of Health strain), is used to construct a recombinant virus containing the coding sequence of the hybrid protein under control of the vaccinia virus "7.5K" promoter (Hue et al., *J. Virol.* 62:176–180 (1988)). The recombinant virus may then be administered intravenously as a vaccine to protect against infection.

In addition to Trp repressor protein, any prokaryotic repressor proteins may be used as the context protein for expressing, in a conformationally restricted manner, a receptor binding site. For example, the MET repressor, bacteriophage lambda repressor phage P22Arc repressor, and the like, can be used in place of the Trp repressor to carry out the invention.

Receptor binding sites for use in the present invention are likewise not limited to those shown in the examples herein, i.e. fibronectin, tenascin, or IFN. Any binding site that recognizes a cell surface receptor for which the amino acid or DNA sequence is known may be used to substitute or insert into the repressor protein to form a hybrid.

The invention described herein further comprises DNA sequences encoding the hybrid monomers previously described. As used herein, the term "DNA sequences" encompasses both double-stranded DNA and single-stranded DNA containing information equivalent to that of the amino acid sequences as determined by the genetic code; such single-stranded sequences can be either in the sense strand orientation or the antisense strand orientation.

A double-stranded DNA sequence encoding a hybrid monomer according to the present invention can be operatively linked to a transcription-effecting DNA sequence capable of effecting transcription of the DNA sequence encoding the monomer. This transcription-effecting sequence is preferably one of *Escherichia coli* Lac promoter, *E. coli* trp promoter, bacteriophage lambda $P_L$ promoter, and tac promoter, a hybrid trp-lac promoter, but other promoters are known in the art and can be used.

This DNA sequence, comprising a DNA sequence encoding a hybrid monomer operatively linked to a transcription-effecting DNA sequence, can be incorporated into a plasmid capable of stably transforming prokaryotic host cells to form a vector. The plasmid preferably has both a drug resistance marker and a replication origin. Many suitable plasmids are known in the art, including, but not limited to, the following: pBR322 and its derivatives; pUC18, pUC19, and their derivatives; bacteriophage μ-derived plasmids, and bacteriophage M13-derived plasmids. Suitable host-vector systems are described, for example, in B. Perbal, "A Practical Guide to Molecular Cloning" (2d ed., John Wiley & Sons, New York, 1988), and "Guide to Molecular Cloning Techniques" (Berger & Kimmel, eds., Academic Press, New York, 1987; Volume 152 of *Methods in Enzymology*). Preferably, the prokaryotic host cells are *E. coli*. Prokaryotic, eukaryotic and archaebacterial host cells stably transformed with such a vector are also within the present invention.

EXAMPLES

The following description provides details of the manner in which particular embodiments of the present invention may be made and used. This description, while exemplary of the present invention, is not to be construed as specifically limiting the invention. Variations and equivalents, now known or later developed, which would be within the understanding and technical competence of one skilled in this art are to be considered as falling within the scope of this invention.

1. Oligonucleotide Design for Producing Trp Aporepressor Hybrid Recombinant DNA

In this invention, surface features of a stable procaryotic aporepressor, in this instance E. coli tryptophan aporepressor (TrpR), are replaced with short oligopeptides that are active as ligands or binding sites for receptors on eucaryotic cells. The procaryotic aporepressor then acts as a scaffold or context protein to allow presentation of the oligopeptide binding site. The nature of the conformation of a receptor binding site can then be evaluated with respect to the specificity of its interactions with its receptor.

To achieve this invention, different regions of the gene encoding TrpR were separately subjected to oligonucleotide-mediated site-directed mutagenesis as described below to produce receptor binding sites in those locations. The nucleotide sequence for a potential integrin binding site derived from human tenascin was engineered into eight different regions on the surface of TrpR. The regions were mutagenized such that a fusion protein having the amino acid residue sequence SRRGDMS (SEQ ID NO 21) flanked by TrpR amino acid residues was produced.

Multiple sites on the TrpR gene which is 324 base pairs in length were chosen to provide a reasonable opportunity to place the engineered recombinant binding site in a variety of structural contexts, one or more of which may be appropriate for receptor binding in the fusion protein. The rationale for selecting particular sites for site-directed mutagenesis was based on the extensive nuclear magnetic resonance (NMR) and X-ray crystallographic characterization of Trp aporepressor protein. See Joachimiak et al., *J. Biol. Chem.*, 258:12641-12643 (1983); Luisi et al., *Biochim. Biophys. Acta.*, 1048:113-126 (1990); and Arrowsmith et al., *Biochem.*, 29:6332 (1990).

Briefly, *E.coli* Trp aporepressor is a small dimeric regulatory protein that binds two molecules of the corepressor, L-tryptophan, to form the active repressor complex. The aporepressor has been crystallized in more than eleven different forms, most of which diffract clearly to a resolution of less than 2 A. The crystal structure of aporepressor reveals that the protein is comprised of six alpha helices joined by short surface turns. Four of these alpha helices, A,B,C, and F, are involved in the formation of an extraordinary stable hydrophobic core; the aporepressor dimer denatures at$>$90° C. The first three helices are intertwined such that many of the van der Waals interactions that stabilize the core of the aporepressor dimer are intermolecular. In addition the alpha-helix F from one monomer makes contacts with both the A and C helices from its partner monomer. The extraordinary stability of the core is emphasized by the fact that the coordinates of atoms in these four-helices vary little from crystal structure to crystal structure.

In contrast, the coordinates of helices D and E vary greatly from structure to structure. When aporepressor and repressor are crystallized in the same space group, the major difference between the two structures is found in the coordinates of helices D and E, leading to a postulate that these two secondary substructures comprise a "flexible reading head" that can interact with DNA when its structure is altered by tryptophan (corepressor) binding. This idea is also a supported by results showing that changes at several critical residues in D (Lys72) and E (Thr81) either abolish DNA-binding, or alter the specificity of the Trp repressor/DNA binding interaction as described by Bass et al., *Science*, 242:240-245 (1988). Two-dimensional NMR analyses of both aporepressor and repressor indicate that "alpha-helix D" is not ordered as a helix in solution although X-ray diffraction analysis indicates that D and E form helix-turn-helix conformation. Both structural models predict that substitutions of a SRRGDMS peptide in between D and E helices will be solvent accessible and unlikely to disrupt the structure of the rest of the TrpR protein.

All synthetic oligonucleotides for use in accomplishing this invention are listed in Table 1 with the corresponding SEQ ID NO. The oligonucleotides were synthesized on an Applied Biosystems DNA synthesizer, model 381A, following the manufacturer's instructions. The use of these oligonucleotides in the construction of TrpR binding site recombinants by site-directed mutagenesis is described in Example 2.

TABLE 1

| | 2 A CC | 3 Q CAA | 4 Q CAA | 5 S TCA | R CGC | (P R CGC | (Y) G GGA | D GAC | M ATG | 8 S TCA | 9 A GCA | 10 A GCG | 11 M ATG | | |
|---|---|---|---|---|---|---|---|---|---|---|---|---|---|---|---|
| TN1 | | 57 I | 58 V | | | | | | | | | | | | |
|  | substitution of 5/2 in N-terminus | | | | | | | | | | | | | | |
| TN2 | ATT | GTC | GAA | GAG | TCA | L R CGC | R CGC | G GGA | E D GAC | E D GAC | M ATG | S AGC | S AGC | R CGT | |
|  | 3 changes; C/D (most conservative substitution) | | | | | | | | | | | | | | |
|  | 59 E | 60 E | 61 L | 62 L | | | | | | | | | | | |
| TN3 | GAA | GAG | CTG | TTG | S TCA | R CGC | E GGA | E D GAC | E D GAC | M ATG | S AGC | Q CAG | R CGT | | |
|  | same 3 changes, end of C (61-62) preserved, 2 residue insertion | | | | | | | | | | | | | | |
|  | 64 G | 65 E | 66 M | 67 S | 69 Q | | | | | | | | | | |
| TN4 | GC | GAA | ATG | AGC | CGC | R CGC | E GGA | L D GAC | K M ATG | N S TCT | E GAA | L CTC | G GGC | 77 A GC | |
|  | 5 changes middle of D loop | | | | | | | | | | | | | | |
|  | 69 R | 70 E | 71 L | 72 K | 74 N | | | | | | | | | | |
| TN5 | CGT | GAG | TTA | AAA | N S TCA | E R CGC | L R CGC | 76 G GGA | A D GAC | G M ATG | 1 S TCC | 80 A GCG | 81 T ACG | 82 I ATT | 83 T AC |
|  | 6 changes, D/E transition | | | | | | | | | | | | | | |
|  | 71 L | 72 N | 73 N | 74 E | | | | | | | | | | | |
| TN6 | TTA | AAA | AAT | GAA | L S TCA | G R CGC | A R CGT | 78 G GGA | I D GAC | A M ATG | T S AGC | 82 I ATT | 83 T ACG | 84 R GCT | 85 G GGA |
|  | 6 changes, D/E transition | | | | | | | | | | | | | | |
|  | 104 L | 105 L | 106 K | 107 S | | | | | | | | | | | |
| TN7 | TTG | CTG | AAA | AGC | (D) R CGC | R CGC | G GGA | D GAC | M ATG | S TCT | X TGA | TTT | TGT | AG | |
|  | substitution 6/1 AT C-term | | | | | | | | | | | | | | |
|  | 30 Y | 31 Q | 32 N | 33 D | | | | | | | | | | | |
| TN8 | C | CAA | AAC | GAT | S TCA | R CGC | R CGC | G GGA | D GAC | M ATG | S TCT | 34 L CTC | 35 H CAT | 36 L TTA | 37 P CC |
|  | 7 amino acid insertion at start of helix B | | | | | | | | | | | | | | |
|  | 2 A | 3 A | 4 Q | 5 Q | | | | | | | | | | | |
| FN1 | G | GCC | CAA | CAA | 5 S TCC | G R CGT | R CGT | (P) G GGA | Y D GAC | S) S AGG | P CCT | 9 A GCA | 10 A GCA | 11 M ATG | 12 A GCA |
|  | substitution of 6/3 in N-terminus | | | | | | | | | | | | | | |
|  | 58 V | 59 E | 60 E | 61 L | | | | | | | | | | | |
| FN2 | GTC | GAA | GAG | CTC | L S TCA | L R CGT | R CGT | 64 G GGA | E D GAC | M S AGG | M S AGG | 68 Q CAG | 69 R CGT | 70 E GAG | 71 L TTA |
|  | 4 changes; C/O | | | | | | | | | | | | | | |
|  | 59 E | 60 E | 61 L | 62 L | | | | | | | | | | | |
| FN3 | GAA | GAG | CTG | TTG | S TCA | G R CGT | 63 E R CGT | 64 G GGA | E D GAC | M S AGG | N P CCT | 68 Q CAG | 69 R CGT | 70 E GAG | |
|  | 3 changes, end of C (61-62) preserved, 2 residue insection | | | | | | | | | | | | | | |
|  | 64 G | 65 E | 66 M | 67 S | 69 Q | | | | | | | | | | |
| FN4 | GGC | GAA | ATG | AGC | G GGA | L R CGT | E R CGT | 76 G GGA | A D GAC | K S AGG | N P CCT | 75 L CTC | 76 G GGC | 77 A GCA | |
|  | 5 changes, middle of D loop | | | | | | | | | | | | | | |
|  | 70 E | 71 L | 72 K | 73 N | | | | | | | | | | | |
| FN5 | GAG | TTA | AAA | AAT | E G GGA | L R CGT | L R CGT | A D GAC | A D GAC | 1 P CCT | 80 A GCG | 81 T ACG | 82 I ATT | 83 T ACG | 71 L TTA |
|  | 5 changes, D/E transition | | | | | | | | | | | | | | |
|  | 73 | 74 | 75 | 76 | A | 78 | I | A | T | 82 | 83 | 84 | 85 | | |

TABLE 1-continued

| | | | | | | | | | | | | | | | | | | | | |
|---|---|---|---|---|---|---|---|---|---|---|---|---|---|---|---|---|---|---|---|---|
| FN6 | N AAT 104 L TTG | E GAA 105 L CTG | L CTC 106 K AAA | G GGA 107 S AGC | R CGT (D) G GGA | G GGA | D GAC | S AGG | P CCT | I ATT | T ACG X TGA | R GCT | G GGA | | | | | | | |
| | 4 changes, D/E transition | | | | | | | | | | | | | | | | | | | |
| FN7 | substitution 6/1 at C-terminus | | | | | | | | | | | | TTT | AGG | | | | | | |
| FN8 | TAC Y 30 | CAA Q 31 | AAC N 32 | GAT D 33 | S TCA | R CGT | G GGA | D GAC | S AGG | P CCT | P CCT | 34 L CTC | 35 H CAT | 36 L TTA | 37 P CC | 7 Y TAT | 8 S TC | | | | |
| | 7 amino acid insertion at start of helix B: | | | | | | | | | | | | | | | | | | | |
| IFN1 | M ATG 1 | A GCC 2 | Q CAA 3 | (Q CAG 4 | L CTG | N AAC | D GAT | L TTC | E GAA | A GCT | C TGT | V) GTA | 5 S TCA | 6 P CCC | 7 Y TAT | | | | | | |
| | insertion 8 residues in N-terminus | | | | | | | | | | | | | | | | | | | |
| IFN2 | K AAT 27 | N A 28 | A V 29 | Y TAC 30 | 31 (Q CAG | L CTG | (n) N GAT | d) L TTC | m E GAA | s) A GCT | C TGT | V) GTA | 34 L CTC | 35 H CAT | 36 L TTA | 37 P CCG | | | | | |
| IFN3 | substitution of 8/2 in A/B turn | | | | | | | | | | | | | | | | | | | |
| | AA E 59 | E GAG 60 | L CTG 61 | TTG 62 | (Q CAG | L CTG | (r) N AAC | g D GAT | e L TTC | s) A GCT | C TGT | V) GTC | 68 Q CAG | 69 R CGT | 70 E GAG | 71 L TT | | | | | |
| IFN4 | substitution 9/5 C/D turn | | | | | | | | | | | | | | | | | | | |
| | E GAA 65 | M ATG 66 | S AGC 67 | Q CAG 68 | r (Q CAG | q L CTG | k D GAT | n L TTC | g E GAA | 1 A GCT | g C TGT | a V) GTA | 78 G GGC | 79 I ATC | 80 A GCG | | | | | | |

2. Preparation of a Recombinant TrpR Plasmid Expression Vector a. Purification of TrpR Gene

A 1.3 kilobase insert from *E. coli* containing the TrpR gene was engineered into a plasmid RPG5, a derivative of pBR322, following procedures described by Gunsalus et al., *J. Bacteriol.*, 140:106-113 (1979) and Gunsalus et al., *Proc., Natl. Acad. Sci.*, 77:7117-7121 (1980). Briefly, MC4100 pheA905 thr:Mu c(Ts) [lambdapl(209) was constructed and a lysate of this lysogen was prepared by UV light induction to infect MC4100 aroF922 fal thr-900 trpR (lambdacI857S7). Lambda thr+transducing phage were recovered and the thr+transductants were assayed for anthranilate synthetase activity for measurement of those carrying the trpR gene. Eco RI restriction digestion fragments from the trpR containing lysogens were ligated into the single Eco RI site of the CM Tc plasmid vector pACYC184. The recipient strain for the transformation was W3110SRT4 and was mutant in trpR. Transformants containing the trpR gene were selected and plasmid DNA was purified following techniques well known to those skilled in the art. Maniatis, Molecular Cloning: A Laboratory Manual, 2 ed, Cold Spring Harbor Laboratory Press, NY, N.Y. (1989). This plasmid was designated pRPG5 and contained the entire TrpR gene. For construction of pPY150 as described below in which the TrpR gene was mutagenized, pRPG5 was first digested with HpaII to form a smaller TrpR gene fragment consisting of 424 bp. Bam HI linkers were constructed on this fragment and then was ligated into a Bam HI linearized pBR322 plasmid. The ligated plasmid containing the smaller TrpR gene was designated pRPG47 and was subsequently digested with Eco RI and Pvu II to form a TrpR gene containing fragment. This fragment was ligated to a similarly digested fragment from plasmid pZ152 described Zagursky et al., *Gene*, 27:183-191 (1984) which contains an M13 origin to form a ligated plasmid which contains the TrpR gene and an M13 origin necessary for subsequent site-directed mutagenesis and helper phage rescue.

b. Insertion of the TrpR Gene-Containing Fragment into an Expression Vector

1) pPY150 Expression Vector

The plasmid expression vector pPY150, a rop+ derivative of pBR322, was used as a recipient cloning vector for insertion of the 424 bp TrpR gene fragment as described in Example 2a. The resulting ligated plasmid carried the M13 origin from pZ152 and a fusion of the PlacUV5 promoter to the TrpR structural gene from pRPG47. The expression of the TrpR was driven from the lacUV5 promoter.

2) pTACTERM Expression Vector

In an alternative to expressing TrpR protein in pPY150, the aporepressor alone or containing a hybrid binding site can be expressed from a rop pBR322 derivative designated pTACTERM 62 which has a stronger tac promoter. The advantage of using pTACTERM over pPY150 is that plasmids replicate to a higher plasmid copy number due to the absence of the rop gene. When expressed from pTACTERM, wild-type TrpR and mutant aporepressors comprise 1 to 5% of the total cell protein. Paluh et al., *Nuc. Acids Res.*, 14:7851-7860 (1986).

In the instant invention, subcloning into pTACTERM was performed following the site-directed mutagenesis procedure for the construction of hybrid TrpR containing receptor binding sites as described below. For the tenascin construct, a 409 bp Bam HI fragment containing the entire TrpR gene and the receptor binding site prepared in Example 3a was subcloned into a Bam HI linearized pTACTERM vector to form a TrpR expression vector as described in Example 6.

3. Preparation of TrpR-Heterologous Receptor Binding Site Recombinant pPY150 Plasmid Vectors a. TrpR Recombinant Hybrids Having an Integrin Receptor Binding Site

1) Tenascin

The tenascin-derived peptide sequence SRRGDMS has been shown to be important in mediating cell binding to the extracellular matrix protein tenascin Bourdon et al., *J. Cell Biol.*, 109:317-330 (1989). The peptide is a competitive inhibitor of specific RGD-dependent receptor binding to tenascin and fibronectin. In addition, antisera specific for SRRGDMS block cell binding to tenascin. Oligonucleotide mediated site-directed mutagenesis was used to introduce nucleotide sequences coding for the SRRGDMS binding site into the TrpR gene in the pPY150 expression vector prepared in Example 2b.

The SRRGDMS sequence was introduced at 8 sites within the TrpR gene. These sites included the amino terminus, a site between alpha-helix A and alpha-helix B, two sites between alpha-C and alpha-D, three sites in alpha-D, or the alpha-D/alpha-E transition, and at the carboxyl-terminus of TrpR. The oligonucleotides used to encode the binding peptide sequence at each site are shown in Table 1. Three substitutions of the SRRGDMS sequence in the D/E transition designated TN4, 5 and 6 were made. Substitution of residues for the region between Lys72 and Thr81 was performed to replace this flexible portion of aporepressor without disrupting the core structure of TrpR. The amino terminal and carboxy terminal sites were chosen because they were solvent exposed, disordered structures as revealed by both NMR and X-ray diffraction data which would likely mimic the active linear synthetic peptides.

The alpha-B helix is between the highly stable alpha-A and alpha-C helices of the hydrophobic core. Substitution of the SRRGDMS sequence at the beginning of alpha-B was determined to not be likely to disrupt core structure but its location between the highly stable structures of the alpha-A and alpha-C would define a particular set of constrained conformations as a result.

The site in alpha-C/alpha-D transition is solvent exposed, but due to its proximity to the hydrophobic core, would provide a unique conformational environment for the SRRGDMS peptide. This SRRGDMS substitution site would be unlikely to disrupt the core structure and limit the ability to obtain NMR data.

Oligonucleotide-mediated site-directed mutagenesis of TrpR pPY150 expression vector was performed by the method described by Kunkel, *Proc. Natl Acad. Sci., USA*, 82:488–492 (1985) using a Muta-Gene In Vitro Mutagenesis Kit (Catalog Number 170-3576, Bio-Rad Laboratories, Richmond, Calif.). The pPY150 plasmid containing the TrpR gene prepared in Example 2bl) was transformed using standard procedures well known to one skilled in the art in the bacterial strain CJ236 (Bio- Rad Laboratories). In an overview of the procedure, this bacterial host strain was deficient for dUTPase and uracil-N-glycosylase which results in an occasional substitution of uracil for thymine in newly synthesized DNA. The resulting DNA, when transformed into a wild-type host with an active uracil-N-glycosylase is inactivated. The uracil-containing DNA was then used as a template for oligonucleotide-mediated site-directed mutagenesis wherein the complementary strand was synthesized using the mutagenic oligonucleotide to prime DNA synthesis. The resultant double-stranded wild-type/mutant heteroduplex molecule was then transformed into a host with an active uracil-N-glycosylase resulting in the inactivation of the uracil-containing wild-type parental strand and the enrichment of the mutant strand.

Briefly, the uracil-containing single-stranded template required for the site-directed mutagenesis procedure was prepared first by maintaining a 5 milliliter (ml) culture of XL1-blue cells (Stratagene, La Jolla, Calif.) containing the pPY150 plasmid at 37° C. for 3 hours. One $\mu$l of a solution containing $1 \times 10^{11}$ plaque forming units (pfu) per ml of M13K07 helper phage provided with the kit was then added to the 5 ml culture and the culture was further maintained at 37° C. for 3 hours. During this time, single-stranded M13 phage containing the single-stranded pPY150 DNA were formed and released from the XL1-blue bacteria.

The bacteria in this culture were killed by heating the culture to 68° C. for 15 minutes. The killed bacteria were removed from culture, by centrifuging the culture at $10,000 \times g$ to produce a supernatant containing the pPY150 single-stranded phage. One ml of this supernatant was added to a previously established 5 ml culture of CJ236 bacteria that was in the late log phase of growth. The culture was maintained at 37° C. for 10 minutes and then 10 microliters ($\mu$l) of the culture was plated onto LB bacterial plates (LB media contains 10 grams/Liter (g/L) of bactotryptone, 5 g/L of yeast extract, 5 g/L of NaCL containing both 50 $\mu$g/ml of ampicillin and 30 $\mu$g/ml of chloramphenicol. The resulting bacterial plates were maintained at 37° C. for 12-18 hours to allow individual colonies of CJ236 bacteria containing the pPY150 single-stranded M13 phage to form.

One of the resulting colonies was selected and used to initiate a 5 ml bacterial culture in superbroth media consisting of 35 g/L bactotryptone, 20 g/L yeast extract, 5 g/L sodium chloride at pH 7.5. This 5 ml culture was maintained at 37° C. for 6 hours and then transferred to 150 mls of superbroth in a 250 ml flask and further maintained at 37° C. for one hour with constant shaking. Then 100 $\mu$l of a solution containing $1 \times 10^{11}$ PFU/ml of M13K07 helper phage (Stratagene) was added to the culture and the culture was maintained at 37° C. for 12-18 hours with constant shaking. During this time, a culture of CJ236 bacteria containing the pPY150 containing TrpK gene single-stranded DNA template was produced.

This culture was then used to isolate the pPY150 single-stranded template using the single-stranded phage DNA isolation procedures described in the p Bluescript II manual (Stratagene). Briefly, 50 $\mu$l of the culture containing pPY150 single-stranded phage produced above was centrifuged at $17,000 \times g$ to produce a clarified supernatant. Approximately 1.2 ml of this supernatant was transferred to an eppendorf centrifuge tube containing 300 $\mu$l of a solution consisting of 3.5 M ammonium acetate at pH 7.5 and 20% polyethylene glycol (PEG). The resulting admixture was maintained at 25° C. for 15 minutes. The admixture was centrifuged at $11,000 \times g$ for 20 minutes to pellet the single-stranded phage present. The resulting supernatant was removed from the phage pellet.

The phage pellet was resuspended in 300 $\mu$l of TE buffer consisting of 10 mM Tris-HCl (Tris [hydroxyl]-aminomethane hydrochloride) pH 8.0 and 1 mM EDTA (ethylene-diamine tetraacetic acid). The resulting solution was admixed with an equal volume of phenol/chloroform and the resulting aqueous phase transferred to a fresh tube. The aqueous phase was reextracted with phenol/chloroform until no significant interface between the organic and aqueous phase was observed. The aqueous phase was then admixed with an equal volume of chloroform and the single-stranded DNA isolated from the aqueous phase by ethanol precipitation using ammonium acetate.

The amount of single-stranded pPY150 DNA isolated was determined by gel electrophoresis. This single-stranded pPY150 DNA was then used as a template in the site-directed mutagenesis procedure below.

The nucleic acid segment coding for the tenascin receptor binding site, SRRGDMS, (SEQ ID NO 45) was then inserted into the plasmide pPY150 using the pPY150 single-stranded DNA template prepared above and the oligonucleotides, TN1 through TN8, listed in Table I in the site directed mutagenesis protocol described in the manufacturer's instructions provided with the Mutagenesis Kit (Bio-Rad). The nucleic acid segment coding for the SRRGDMS was placed at eight different locations within the pPY150 template DNA.

Five ug of the pPY150 single-stranded template prepared above were admixed with 50 ng of each of the oligonucleotides, TN1 through TN8, to form a 10 ul admixture. The admixture was maintained for 10 minutes at 68° C. followed by 5 minutes at 25° C. to allow the oligonucleotide to anneal to the single-stranded template. The complementary strand was then synthesized by admixing 4 ul of a solution containing 10 mM of adenosine triphosphate (ATP), 4 ul of a buffer containing 0.66 M Tris-HCl at pH 7.6, 50 mM MgCl$_2$, 50 mM dithiothreitol (DTT), 2 ul of a solution containing 2.5 mM each of dCTP, dATP, dGTP, and dTTP, 1 ul of T4 DNA ligase (Stratagene) and 1 ul of the Klenow fragment of DNA Polymerase I (Stratagene) to form a mutagenesis reaction admixture. The mutagenesis reaction was terminated by admixing 1 ul of 50 mM EDTA. The resultant mutagenized closed circular cDNA was then transformed into competent CG103F' Fan bacteria (Bio-Rad) and kanamycin resistant clones containing the mutagenized DNA were selected. DNA was then isolated from the resulting transformants using the DNA isolation procedures of Sambrook et al., *Molecular Cloning: A Laboratory Manual, Second Edition*, Cold Spring Harbor Laboratory, Cold Spring Harbor, New York, N.Y. (1989). The presence of mutations were confirmed by dideoxynucleotide sequencing of the isolated double stranded DNA using the manufacturer's instructions in the AMV Reverse Transcriptase $^{35}$S-dATP Sequencing Kit (Stratagene).

Following site-directed mutagenesis and verification of the construction of the hybrid TrpR-SRRGDMS-containing plasmid, the region containing the entire mutagenized TrpR gene was subcloned into a pTAC-TERM expression vector for expression of the hybrid protein as described in Example 6.

2) Fibronectin

A peptide, GRGDSP (SEQ ID NO 46), derived from the extracellular matrix protein fibronectin containing the integrin receptor binding site RGD has been described. Pierschbacher et al., *J. Cell Biol.*, 28:115–126 (1985). The receptors alpha 5 beta$_1$, alpha, beta$_1$, alpha, beta$_5$, for example recognize an RGD-binding site in matrix ligands. The receptors have overlapping but distinct ligand specificities. Peptides from fibronectin (GRGDSP) or tenascin (SRRGDMS) act as competitive inhibitors of receptors binding fibronectin, tenascin and vitronectin and GRGDS (SEQ ID NO 46) peptides can inhibit tumor metastasis, tumor invasiveness and in vitro angiogenesis. The peptides do not have, however, the receptor specificity of the natural matrix ligand. Conformation must play an integral role in receptor recognition of the RGD binding sites. This has important implications since this conformational recognition can result in very distinct cellular responses. Fibronectin is a strong cell adhesion and spreading factor, while tenascin prompts reduces cell adhesion and increased motility but not spreading. The two proteins contrast and complement each other in modulating adhesion and cell motility.

The GRGDSP sequence is placed at the same sites as with the tenascin peptide in TrpR as described in Example 3a1). Oligonucleotide-mediated site-directed mutagenesis is performed as described using the fibronectin binding-site encoding oligonucleotides listed in Table 1. The resulting TrpR-GRGDSP hybrid constructs are then subcloned as described in Example 6 into a pTAC-TERM expression vector for expression of the hybrid protein. The expressed hybrid protein is then assayed for binding to fibronectin receptors as described for tenascin receptors in Example 7.

b. TrpR Recombinant Hybrids Having a Lymphocyte Receptor Binding Site, CR2

1) Alpha Interferon (IFNa)

The peptide QLNDLEACV (SEQ ID NO 47) is the receptor binding site on IFNa which is recognized by the B lymphocyte receptor called CR2. Oligonucleotide-mediated site-directed mutagenesis was performed as described using the interferon binding-site encoding oligonucleotides listed in Table 1. The resulting TrpR-GRGDSP hybrid constructs were then subcloned as described into a pTACTERM expression vector as described in Example 6 for expression of the hybrid protein. The expressed hybrid protein was then assayed for binding to fibronectin receptors as described in Example 8.

4. Preparation of TrpR-Heterologous Receptor Binding Site Recombinants to Produce Cysteine Disulfide Loops a. TrpR Recombinant Hybrids Having an Integrin Receptor Binding Site Containing Cysteine Disulfide Loops The conformational context of the SRRGDMS (SEQ ID NO 21) or GRGDSP (SEQ ID NO 46) sequence within TrpR is further altered by creating cysteine disulfide bridges to create a loop containing the binding site sequence. The rationale for this is several fold. First, modeling predictions (Cachau et al., *J. Mol. Res.*, 2:179–186 (1989)) and results with cyclic peptides (Pierschbacher et al., *J. Biol. Chem.*, 262:17294–17298 (1987)) and a helical dimers (Engel et al., *Bichem.*, 30:3161–3169 (1991)) indicate that the most active conformations are likely to be contained in a turn structures or loops. Second, the snake venom disintegrin proteins have the RGD site flanked by cysteines (Gould et al., P.S.E.B.M., 195:168–171 (1990)). Third, the active TrpR-TN5 hybrid protein produced in Example 6 is likely to reside within an extended or loop structure. Finally, cysteine disulfide bridges constrain the binding sequence in ways not possible through the TrpR context alone. By selecting the flanking distance from the binding sequence, loops of various sizes and varying conformation contexts are generated. The formation of disulfide bridges is analogous to the formation of artificial cyclic peptides. However, unlike cyclic peptides the NH$_2$ and COOH protein context is not lost.

This strategy is most applicable to TrpR-hybrids at the NH$_2$ and COOH-termini (TrpR-TN1, TrpR-TN7) and D/E transition (TrpR-TN4, TN5, and TN6), because these sites are flexible regions of Trp aporepressor and changes in these regions are least likely to disrupt the hydrophobic core. Core disruption would make NMR spectroscopy and X-ray crystallographic analysis exceedingly difficult. Because both TrpR-Tn1 (NH$_2$-terminal) and TrpR-TN5 (D/E) are both active receptor binding proteins, cysteine bridges in these mutants are generated first. Cysteine pairs flanking the SRRGDMS sequence are introduced into the TrpR-TN1 and TN5 by a single round of site-directed mutagenesis as described in Example 3 using paired oligonucleotides coding for a cysteines flanking the SRRGDMS substitution site. The oligonucleotides used for generating hybrid TrpR-SRRGDMS fusion proteins having disulfide loops are listed in Table 2 below.

TABLE 2

CYS-CYS LOOPS:
SSL 1A(TN1) (SEQ ID NO 48)

| 1 | 2 | 3 | | | | | | | | 10 | 11 | 12 |
|---|---|---|---|---|---|---|---|---|---|----|----|----|
| M | A | Q | C | S | R | R | G | D | M | S | C | A | M | A |
| ATT | ATG | GCC | CAA | TGC | TCA | CGC | CGC | GGA | GGC | ATG | TCA | TGC | GCA | ATG | GCA |

SSL 1Ba(TN1) (SEQ ID NO 49)

| | | 1 | | 3 | 4 | | |
|---|---|---|---|---|---|---|---|
| | | M | C | Q | Q | S | R |
| CGA | CAT | ATT | ATG | TGC | CAA | CAA | TCA | CGC |

SSL1 Bb(TN1) (SEQ ID NO 50)

| 8 | 9 | 10 | | 12 | 13 | 14 | 15 |
|---|---|----|---|----|----|----|----|
| M | S | A | A | C | A | E | Q | R |
| ATG | TCA | GCA | GCG | TGC | GCA | GAA | CAG | CGT |

SSL 5A(TN5) (SEQ ID NO 51)

| 68 | 69 | 70 | 71 | | | | | | | | 81 | 82 | 83 | 8 |
|----|----|----|----|---|---|---|---|---|---|---|----|----|----|---|
| Q | R | E | L | C | S | R | R | G | D | M | S | C | T | I | T |
| CAG | CGT | GAG | TTA | TGC | TCA | CGC | CGC | GGA | GAC | ATG | TCC | TGC | ACG | ATT | ACG | CG |

SSL5 Bb(TN5) (SEQ ID NO 52)

TABLE 2-continued

| 66 | 67 | 68 | 69 | | 71 | 72 | | |
|---|---|---|---|---|---|---|---|---|
| M | S | Q | R | C | L | K | S | R |
| ATG | AGC | CAG | CGT | TGC | TTA | AAA | TCA | CGC |
| SSL5 Bb(TN5) (SEQ ID NO 53) | | | | | | | | |
| | | 80 | 81 | | 83 | 84 | 85 | 86 |
| M | S | A | T | C | T | R | G | S |
| ATG | TCC | GCG | ACG | TGC | AGC | GCT | GGA | TCT |

The TrpR-TN1 gene is substituted with cysteines at residues 4 and 9, to create a 7 residue loop, and with cysteines at residues 2 and 11, to form an 11 residue loop. The TrpR-TN5 gene is mutated to substitute cysteine at residues 72 and 80 flanking the SRRGDMS sequence and again at residues 70 and 82 to produce a larger loop. Disulfide bonds of the purified proteins will be formed by in the presence of thioredoxine and glutathione as described by Pigiet et al., *Proc. Natl. Acad. Sci., USA*, 83:7643–7646 (1986). The activity of the TrpR cysteine loop proteins is then assayed for cellular and direct receptor binding in both their disulfide and reduced forms.

5. Preparation of TrpR-Heterologous Receptor Binding Site Recombinants to Produce Variant Peptide and the binding site. For example, to mutagenize the context of the SRRGDMS binding site in TrpR-TN5, the codons for the two residues (LK SRRGDMS AT) flanking the SRRGDMS sequence are changed. By this means, many amino acid substitutions are generated rapidly with a few oligonucleotides as shown in Table 3 below. Double mutants at both positions are generated with a single round of mutagenesis using two different primers, or one large primer. DNA sequence characterization of the mutants are then analyzed quickly by PCR sequencing of bacterial colonies (Ruano et al., *Proc. Natl. Acad. Sci., USA*, 88:2815–2819 (1991)). TrpR-mutant products (1–10 mg) are then isolated from 500 ml to 2 liter cultures and analyzed preliminarily for cell binding and receptor binding activities as described in Example 7.

TABLE 3

FLANKING CHANGES FROM TN5:

STARTING SEQUENCE:
```
      S   Q   R   E   L   K   S   R   R   G   D   M   S   A   T   I   T   R   G
      AGC CAG CGT GAG TTA AAA TCA CGC CGC GGA GAC ATG TTC GCG ACG ATT ACG CGT GGA

CXA1  CGT GAG TTA AAA NNS NNS CGC GGA GAC NNS NNS GCG ACG ATT ACG
CXA2  CGT GAG TTA AAA NNS CGC CGC GGA GAC ATG NNS GCG ACG ATT ACG
CXA3  CGT GAG TTA AAA TCA NNS CGC GGA GAC NNS TCC GCG ACG ATT ACG
CXA4  AGC CAG CGT GAG NNS NNS TCA CGC CGC GGA GAC ATG TCC NNS NNS ATT ACG CGT GGA
```

Starting sequence is SEQ ID NO 54
CXA1, CXA2, CXA3, and CXA4 have the respective SEQ ID NO 55 through 58

Flanking Sequences a. TrpR Recombinant Hybrids Having an Integrin Receptor Binding Site Site-directed mutagenesis of ligand peptide and flanking sequences is performed as described in Example 3 to answer two kinds of questions. First, by altering residues within a binding site one at a time, which primary features of a binding site are critical for function and which substitutions are allowed can be determined. Second, single or multiple residues immediately flanking the grafted site can be changed which may alter the conformation and receptor specificity of the ligand binding site. These mutants represent the third level of mutagenesis that will allow the alteration of the SRRGDMS conformation. Because this level of sequence alterations generates the most mutants with the least predictability as to results, site-mutagenesis as described below will be performed on those TrpR-SRRGDMS or GRGDSP recombinant proteins that prove most active and for which sufficient structural and functional data are available to assist in our experimental design. This approach will allow the "fine tuning" of a binding site context with respect to receptor binding.

Alterations in amino acids flanking the receptor binding site are made by site-directed mutagenesis as described by Kunkel, supra and in Example 3. The mutagenesis products are screened by two approaches. The first approach is to prepare oligonucleotide primers with degenerate sequences to obtain multiple codon mutations for amino acid positions immediately flanking A second screening method is for the detection of active recombinant protein mutants by labeled receptor binding on nitrocellulose or immobilon-p colony lifts. The filters are heated to 85° C. to break open cells and denature proteins as many of the TrpR-SRRGDMS are heat stable. Filters are then blocked with 1 mg/ml bovine serum albumin in phosphate-buffered saline (BSA-PBS) prior to addition of cells or purified receptor. Cells or labeled receptor are used to detect active receptor binding protein in producing colonies. An alterative is to French press (lyse) 5 ml over night cultures, spin down membranes and coat microtiter wells for cell attachment. This assay has been used to analyze bacterial invasion for an integrin binding protein necessary for *Y. pseudotuberculosis* invasion of mammalian cells (Isberg et al., *Proc. Natl. Acad. Sci., USA*, 85:6682–6686 (1986)). This procedure could greatly increase the ability to rapidly screen many mutants at each site.

While it is very easy to generate 19 mutants at each of the amino acid residues flanking the binding site sequence, criteria are needed to set priorities for the analysis of flanking sequence mutants. Such criteria are difficult to assign a priori since side chain structure, charge, bond angles, and freedom of rotation, may all play a role in conformation affects on the adjacent SRRGDMS sequence and cannot be reliably predicted. In addition, some amino acids substitutions may have no effect, while others may have the same effect. For example changes to aromatic amino acids or proline might be expected to alter helical structures and tend to fix turns. It may be desirable to design flanking helical or α structures by multiple amino acid substitutions in D and/or E helices. The strength of genetic engineering is that such sequence alterations once decided on are very simple and rapid to do. Finally, the results of NMR and X-ray studies of TrpR-TN5 will allow molecular modeling to be used to make predictions as to the effects of a given flanking amino acid substitution on the SRRGDMS conformation, and will help the selection of the top priority hybrids for analysis.

b. TrpR Recombinant Hybrids Having a CR2 Lymohocyte Receptor Binding Site

The IFNa site has a Cys residue and therefore, substitutions of the Cys in the binding site with four conservative amino acid residue changes (Ser, Ala, Tyr, and Val; (Dayhoff, *Atlas of Protein Sequence and Structure* Vol. 5, suppl. 3 (1978)) are made to determine the effects on its specific activity If the Cys residue is essential, one of several different alternative approaches for making aggregates of the monomeric hybrid proteins is adopted. For example, the protein is reacted with N-hydroxysuccinimido-biotin (which attacks free Lys residues), then reacted with the derivatized protein with streptavidin beads. Even if a hybrid protein is constructed with both a Cys residue in the binding site and a second, terminal Cys residue, it is likely that the terminal Cys residue will be more solvent-exposed and reactive, and mild oxidation will favor the tethering of the protein to a solid support over the attachment of the site.

6. Preparation of pTACTERM Expression Vector and the Expression of TrpR-Heterologous Receptor Binding Site Fusion Proteins a. Insertion of TrpR-Heterologous Fragment into pTACTERM

After site-directed mutagenesis for the insertion of receptor binding sites into the TrpR gene as prepared in Example 3, the pPY150 plasmid containing the mutated region was restriction digested with Bam HI resulting in the isolation of a 424 bp fragment. The fragment consisted of one the TrpP genes mutagenized at one eight different sites with either the peptide for the receptor binding site of tenascin, fibronectin and alpha interferon. The isolated 424 bp fragment was then inserted into a Bam HI linearized pTACTERM plasmid expression vector which contained a tac promotor/operator and rpoC transcription terminator. A schematic of the construction of a pTACTERM expression vector containing the TrpR gene mutagenized with the tenascin peptide is shown in FIG. 1.

The resulting pTACTERM TrpR-Heterologous receptor binding site hybrid was then transformed into CE103F' bacteria as described in Example 3. Kanamycin resistant transformants containing the pTACTERM plasmid were selected and analyzed for hybrid constructs as described in Example 3.

a. Expression and Purification of a Hybrid TrpR-SRRGDMS Fusion Protein from pTACTERM Hybrid fusion proteins were expressed from the selected pTACTERM expression vectors prepared above following the procedure described by Paluh et al., supra. Individual transformants were selected which contained a pTACTERM expression plasmid in which the TrpR gene was mutagenized with the SRGGDMS peptide at the N-terminus designated as Trp-TN1 (TN1 as shown in Table 3 and at the D/E helical transition designated as Trp-TN5 (TN5 as shown in Table 3). For the expression of these two fusion proteins, a single transformant colony was picked from the LB-Kananmycin plate and inoculated into a 10 ml culture of minimal medium containing 0.2% glucose, 0.1% acid casein hydrolysate, 0.1% yeast extract and 200 ug/ml ampicillin. After maintaining the culture overnight at 37C, the culture was admixed with 1 liter of fresh medium prepared as above containing 0.4% glucose. The culture was maintained until the bacterial culture grew to a density of about $4 \times 10^8$ cells/ml. A filter-sterilized solution of 0.1 M isopropylthiogalactopyranoside (IPTG) was admixed to a final concentration of 1 mM to initiate induction of the fusion protein from the tac promoter. The culture was then shaken overnight at 37° C. and the cells were harvested by centrifugation at $3000 \times g$. The final yield was 3 to 5 grams of cells/liter.

To purify the TrpR-SRRGDMS fusion protein, forty-five grams of cells produced above were suspended in 225 ml of 0.1 M Tris-HCl at pH 7.6 and disrupted by sonic oscillation. The resulting cell extract was centrifuged for 20 minutes at $29,700 \times g$ at 4C. The resultant supernatant was removed and streptomycin sulfate (20%) was admixed to 1% with stirring. The supernatant was stirred for 30 minutes and the admixture was brought to 62° C. by shaking in a flask in a 66° C. water bath for approximately 5 minuets and then shaken for an additional 5 minutes. The admixture was then chilled on ice and the precipitate was removed by centrifugation for 10 minutes at $36,400 \times g$. Solid ammonium sulfate was admixed to the supernatant to 45% saturation, the mixture was stirred in an ice bath for 45 minutes and, after centrifugation, the supernatants were collected. Ammonium sulfate was admixed to 70% saturation and the mixture was stirred for 1 hour. The precipitate was collected by centrifugation.

The 45-70% ammonium sulfate precipitate containing the fusion protein was dissolved in 10 mM sodium phosphate at pH 7.6 containing 0.1 mM EDTA and 0.1 M NaCl to form a fusion protein solution. The solution was dialyzed overnight against the same buffer. The resultant dialyzed solution was then applied to a Whatman P11 phosphocellulose column equilibrated with the same buffer. The column was washed with about 20 ml of P11 buffer and then the immobilized proteins were eluted with a gradient containing 80 ml of 10 mM sodium phosphate at pH 7.6 containing 0.1 mM EDTA and 0.15 M NaCl in the first mixing flask and 160 ml of the buffer with 0.75 M NaCl in the second flask. The cross-sectional area of the second flask was twice that of the mixing flask. Repressor eluted in a sharp peak in the middle of the gradient. The overall yield obtained in the peak fractions was 25-50 mg pure hybrid fusion protein, TrpR-SRRGDMS, per liter of cells.

Rapid batch-elution steps from heparin-agarose, DEAE-5PW or Fast-Q followed by Cibacron-blue-agarose chromatography have also been used as steps in the purification of TrpR-hybrid proteins Although hybrid proteins may have different elution profiles from these resins, it is likely they will bind, and be batch eluted. Both TrpR-TN1 ($NH_2$-terminus) and Trp-R-TN5 (D/E transition) mutants were isolated by these procedures.

7. Analysis of Cell Binding to TrpR-SRRGDMS Fusion Protein a. Cell Attachment Assays

Recombinant proteins were assessed for cell binding activity in a microtiter plate cell attachment assay. The assay is a simple and rapid means of assessing cell binding to the recombinant protein. In addition the specificity of the interaction is explored with specific inhibitor peptides, recombinant proteins and matrix proteins. Finally, the assay is used to screen a variety of cell lines to determine the range of cell types capable of interacting with the recombinant protein.

The assay used was a modification of one widely used in the field. See Bourdon et al., *J. Cell Biol.*, 108:1149–1155 (1989). In the assay, wells of a 96-well microtiter plate were coated with the purified fusion proteins, TrpR-TN1 or TrpR-TN5, at concentrations ranging from less than 1 ug/ml protein to 20 ug/ml protein. Nonspecific sites on the well were blocked with BSA. Human tumor cells, U251MG-human glioma or MG63-human sarcoma having the receptor which binds the SRRGDMS receptor binding site with or without inhibitor were added and allowed to adhere for 30 to 90 minutes at 37° C. Following the maintenance period, non-adherent cells were washed out and relative numbers of adherent cells were determined. The assay can detect binding interactions in the absence of extensive cell spreading.

In the cell attachment assay, the attached cells stained with Di-I a vital fluorescent dye which intercalates in cell membranes. The advantages of this form of cell tagging are that cells can be rapidly labeled, the label remains cell bound, it is not radioactive, and it is easily detected in a fluorescence plate reader.

Proteins displaying positive cell attachment were tested at least three times in separate assays. Results of cell attachment assays will provide analysis of whether the recombinant protein supported cell binding, provided a dose response curve from which to determine coating concentrations for inhibition assays and gave some indication if there were cell line differences in attachment to the coated protein. Because a great deal is known about the repertoire of integrin receptors on the cell surfaces of these cell lives using receptor subunit specific antibodies, any striking difference in cell attachment activity could provide clues as to the receptor involved.

Figure 2:
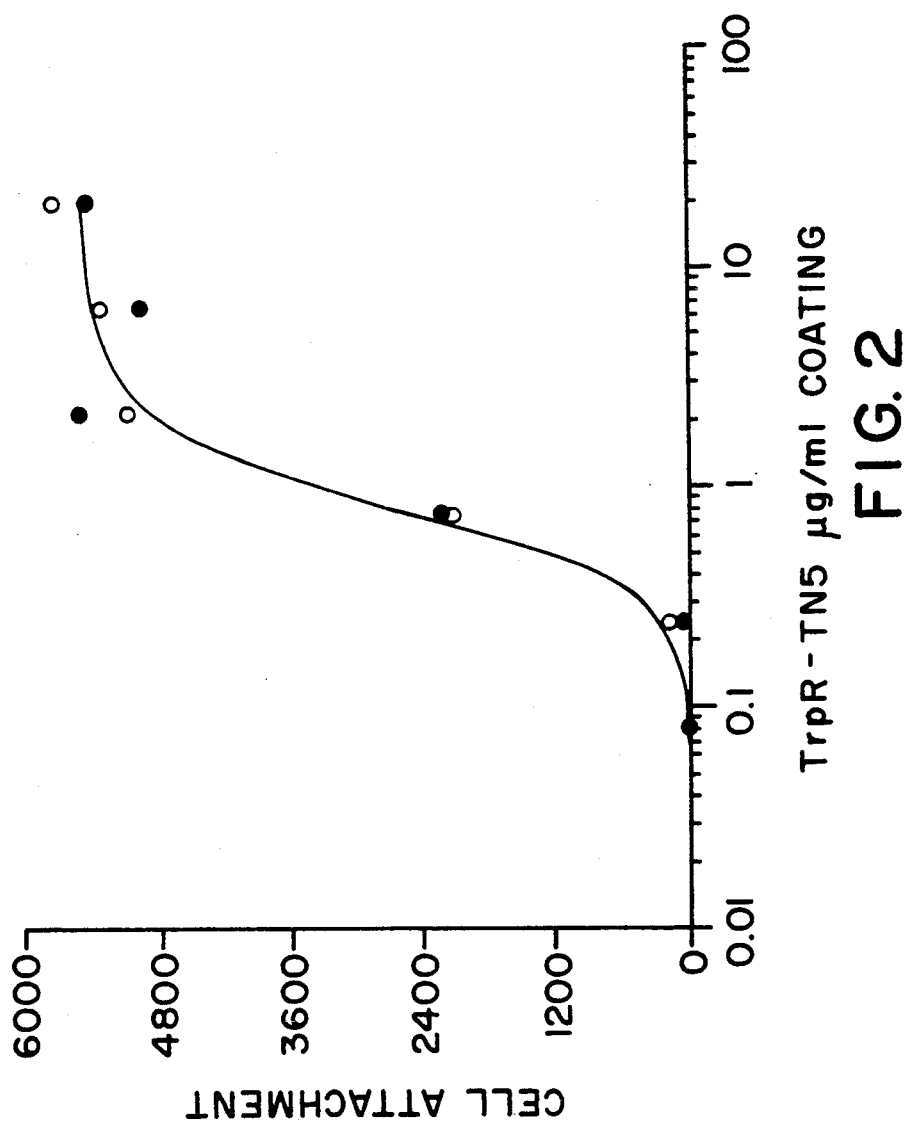

In cell attachment assays to two TrpR-SRRGDMS hybrids, TrpR-TN1 and TrpR-TN5, U251MG cells adhered in a saturable manner to increasing concentrations of TrpR-TN5-coated wells saturating at approximately 2 ug/ml protein as shown in FIG. 2. Additional cell attachment assays revealed that both the TrpR-TN5 and TrpR-TN1 fusion proteins supported cell attachment while the wild-type TrpR did not as shown in FIG. 3.

Specificity of cell attachment was then determined in competition assays of cell attachment using SRRGDMS or GRGDSP peptides as competitive inhibitors of recombinant protein cell attachment. In the presence of 1 mg/ml SRRGDMS peptide, the specific attachment of U251MG cells to either fusion protein was inhibited as shown in FIG. 3.

Figure 3:
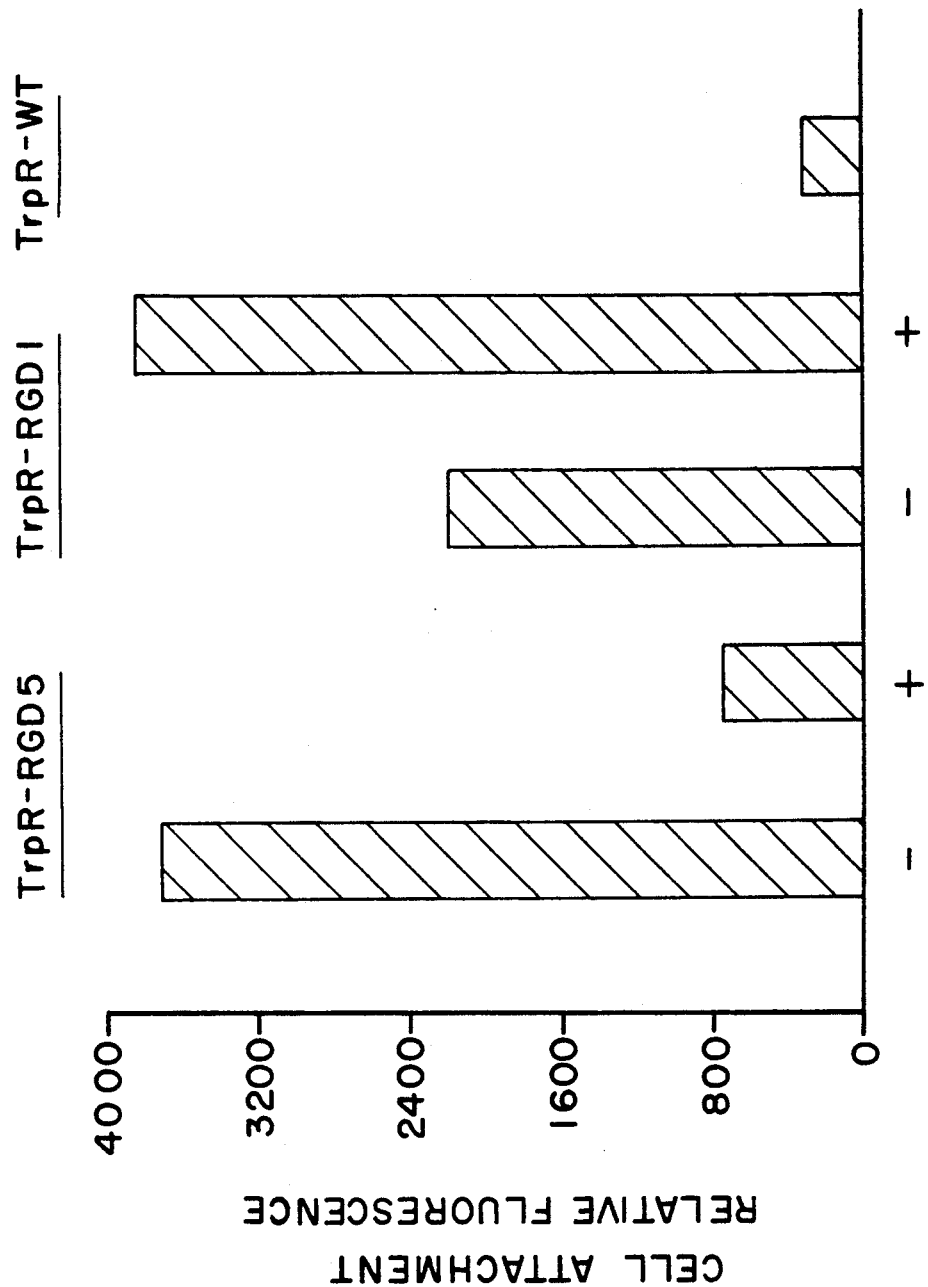
Figure 4:
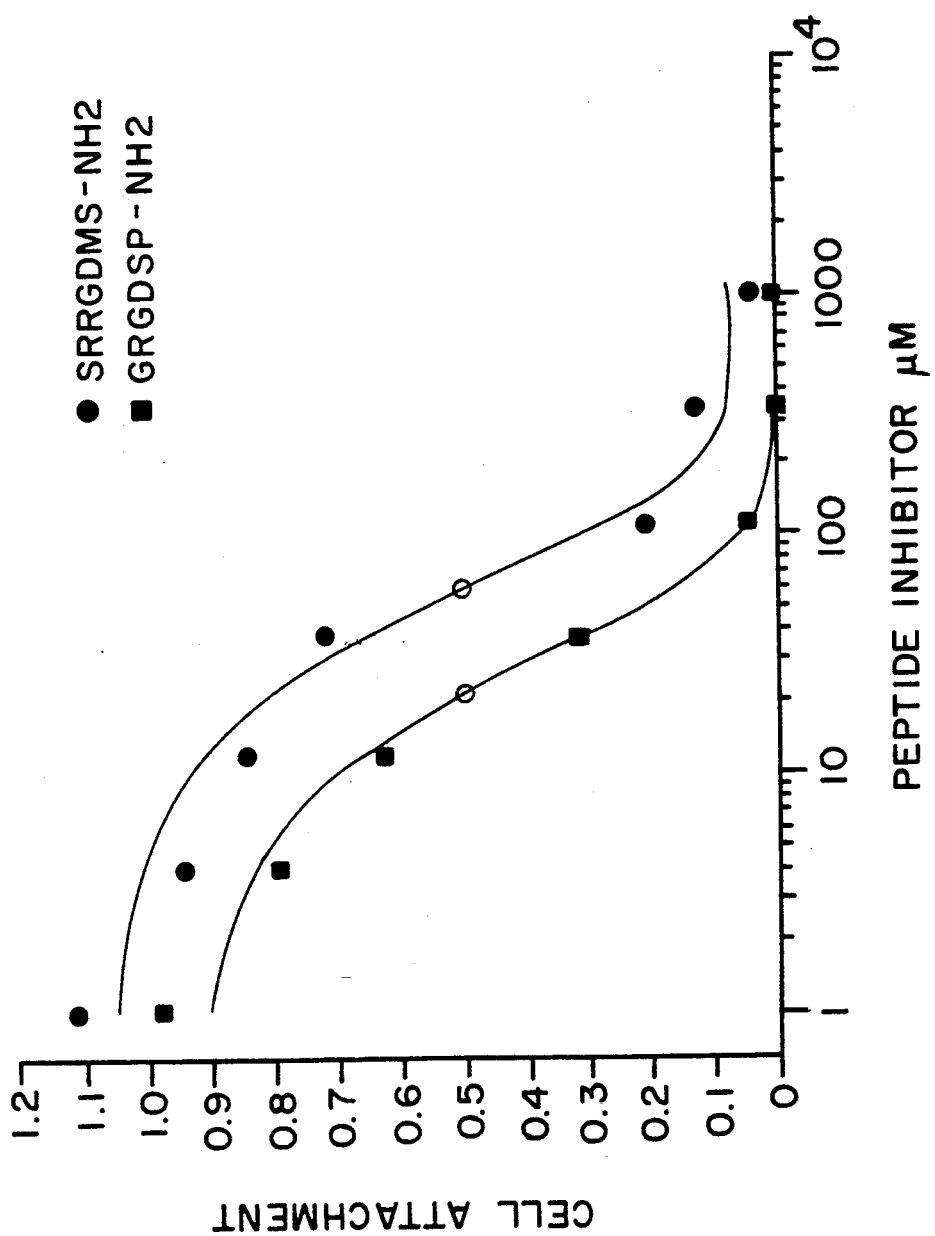

In these experiments, cell attachment to TrpR-TN5 was inhibited by the peptides SRRGDMS and GRGDSP at 1 mg/ml but not by several control peptides including a scrambled sequence derived from the SRRGDMS peptide sequence (MGSRSRD) (FIG. 3). Cell attachment to TrpR-TN1 was enhanced in the presence of SRRGDMS peptide over the range of TrpR-TN1 coatings tested. Inhibition curves of TrpR-TN5 cell attachment with either SRRGDMS or the GRGDSP peptide indicated that they have similar potency as inhibitors of TrpR-TN5 mediated cell attachment. The IC50 values for the two peptides is in the range of 20 to 60 uM (FIG. 4). The IC50 of TrpR-TN5 is approximately 5 uM. The RGD-mediated cell attachment activity of the TrpR mutants TN5 and TN1 have been shown to not be restricted to the cell line initially used; these proteins also mediated cell attachment to a second tumor cell line MG63 and the fibroblast line, SDB.

The fusion proteins were also evaluated in their ability to promote cell spreading which is an indicator of appropriate receptor-mediated signalling following specific ligand interaction. The cell attachment assays were performed as described above and cell morphology was visualized microscopically 30 minutes after plating on the fusion protein-coated wells. Both TrpR-TN1 and TrpR-TN5 promoted rapid spreading of adherent cells in contrast to BSA-coated wells.

b. Receptor Isolation and Characterization

The receptor or receptors that may be interacting with the TrpR-TN5 protein were isolated through the use of an TrpR-TN5 affinity column. The TrpR-TN5 fusion protein produces in Example 6 was coupled to cyanogen bromide activated sepharose and the resulting affinity column was used to isolate receptor from $^{125}I$ radiolabeled cell surface membrane preparations from the U251 cell line. The labelled cells were solubilized in octylglucoside (25 mM) and the extract was passed over TrpR-TN5-sepharose. Bound protein was eluted with 20 mM EDTA. Radiolabeled proteins were immunoprecipitated with 442 anti Beta 1 antibody, LM 142 anti-alpha v antibody and LM 609 anti-alpha v and beta 3 complex antibody.

The results indicate that at least three proteins bound on the affinity column. These proteins appeared to have the SDS-PAGE mobility characteristics of an 140 kd alpha subunit and $beta_1$, $beta_3$, and $beta_5$, integrin subunits. These receptors were characterized using immunoprecipitation with specific antibodies to integrin alpha and beta subunits. Immunoprecipitation of the receptor pool with LM142 anti $alpha_v$ monoclonal antibody showed that the majority of the receptor binding to TrpR-TN5 had an $alpha_v$ subunit. The antibody cannot distinguish between two possible beta subunits, $beta_3$ and $beta_5$. The $alpha_v$, $beta_3$ and $beta_5$ receptors recognized the sequence RGD in the adhesion proteins fibronectin and vitronectin as well as RGD peptides. Immunoprecipitation with LM609, an $alpha_v$ and beta 3 complex specific monoclonal antibody demonstrate that the major receptor subunits correspond to $alpha_v beta_3$.

This result was supported by both liposome assays and cell adhesion blocking experiments. The liposome binding assay as described by Pytela et al., *Proc. Natl. Acad. Sci., USA*, 82:5766–5770 (1985) was used to directly determine if receptors reconstituted in liposomes bound to immobilized ligand. The receptors $alpha_1 beta_1$, $alpha_5 beta_1$, $alpha_3 beta_1$, and $alpha_v beta_3$, $alpha_v beta_5$, were purified on ligand affinity columns as described above. Liposomes were prepared by dialyzing mixtures of receptor in octylglucoside with phosphatidylcholine (PC) and $^3$H-PC, placed on ligand-coated plates, and allowed to bind. Ligands included TrpR-SRRGDMS hybrid, TN, FN, LN, VN, and Fb, SRRGDMS-BSA and GRGDSP-BSA. Controls included BSA and control peptide-BSA conjugates. The $^3$H-PC was measured in washed wells, by solubilizing bound counts in 1% SDS and counting in a beta-counter.

Figure 5:
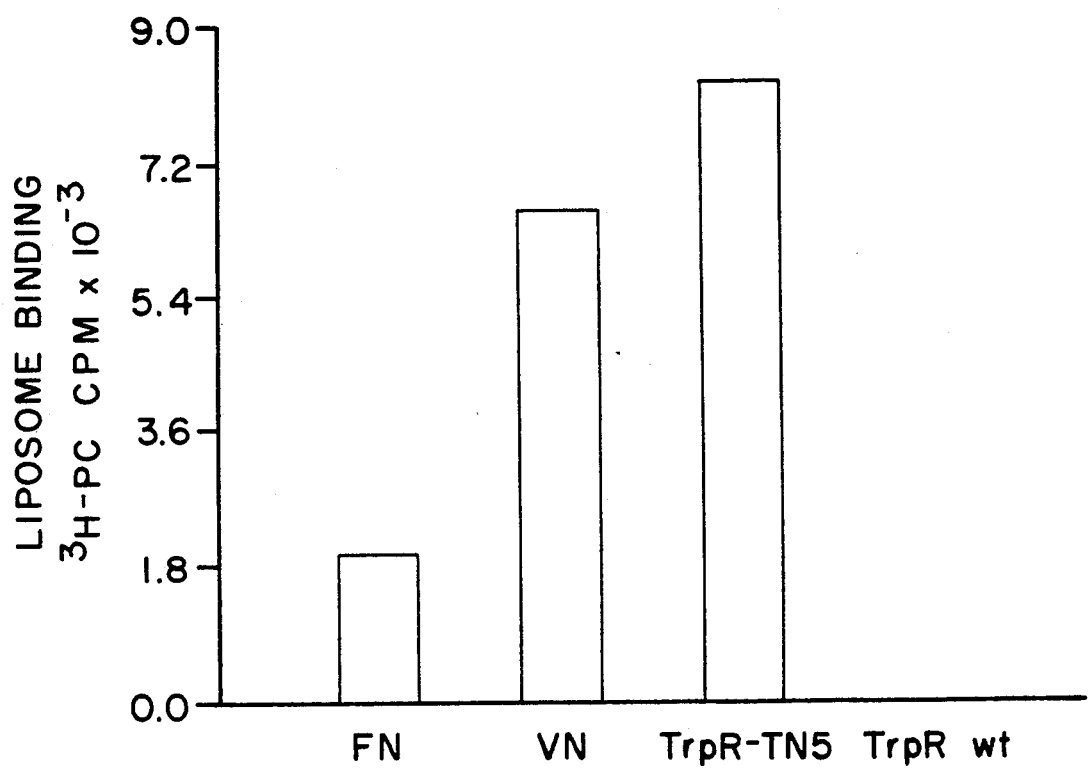

Results of liposome binding assays with alpha$_v$ and beta$_{3,5}$ isolated from an GRGDSP-sepharose column showed high levels of binding to TrpR-TN5 (FIG. 5).

Figure 6:
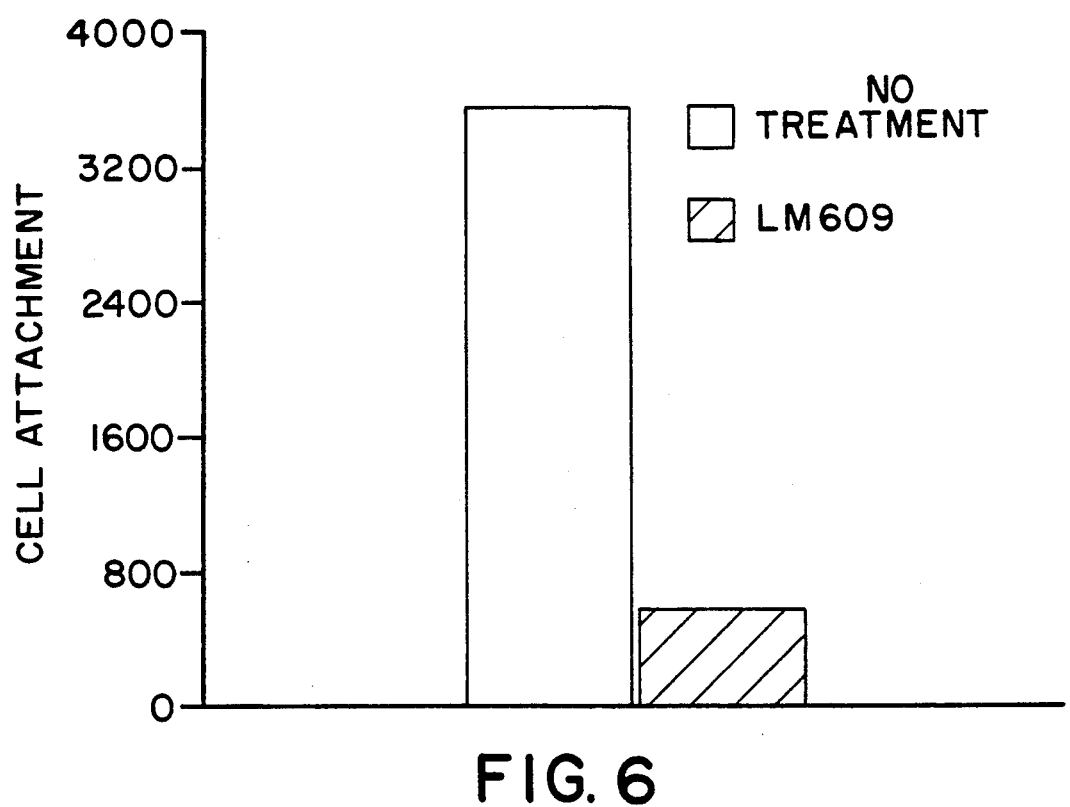

Cell attachment to TrpR-TN5 was completely inhibited by the alpha$_v$ beta$_3$ blocking monoclonal antibody LM609 (FIG. 6). These results showed that the TrpR-TN5 protein is a receptor binding site for the alpha$_v$ beta$_3$ receptor.

In addition to the major alpha$_v$beta$_3$ receptor an additional beta$_1$ receptor (or receptors) appears capable of binding to TrpR-TN5 as shown by immunoprecipitation of receptor heterodimer with monoclonal antibody 442 anti beta$_1$. The alpha subunit does not appear to be alpha$_v$ since LM142 did not immunoprecipitate detectable alpha$_1$ from the affinity purified receptor pool.

These results are significant because they demonstrate that the TrpR-TN$_1$ and TrpR-TN5 hybrid fusion proteins are biologically active in mediating RGD-dependent integrin binding and cell spreading. The results demonstrate that the SRRGDMS sequence can be substituted or grafted on the TrpR protein and confer integrin mediated cell adhesion activity on the recombinant protein.

8. Nuclear Magnetic Resonance Spectroscopy of TrpR-SRRGDMS Hybrid Fusion Proteins Preliminary conformational data on the recombinant Trp-TN5 prepared in Example 6 has been obtained. Most of the proton NMR signals of trp-repressor and aporepressor have been assigned to their respective residues in this protein dimer. See Arrowsmith et al., Biochem., 29:6332 (1990). Based on these assignments and nuclear Overhauser effect (NOE) data, low resolution structures of both forms of the protein have been determined in solution. The data show that the helices ABC and F of trp-repressor in solution formed a highly stable and compact central core. The regions which correspond to helices D and E in the crystal structure, however, appeared to be independent flexible regions in solution, as reflected by the rate at which their amide protons exchange with solvent. For this reason a substitution of helix D for a peptide of similar length should have little effect on the structure and chemical shifts of the remaining parts of the protein.

The 2D COSY spectrum of wild-type trp-repressor (A) with (a less concentrated sample) of TN% (B) reflected the folded tertiary structure of the protein in both samples. For instance, the somewhat unusual chemical shifts of the methyl groups of V55 and L34 reflect the packing of helices A with C and B with F, respectively. V55 of helix C contacts the aromatic ring of F22 in helix A of the opposite subunit, and L34 of alphaB contacts W99 in alphaF of the opposite subunit. The contacts with these aromatic rings give rise to the unusual chemical shifts. These characteristic peaks are identical in the two proteins (as are most others) indicating that the structural integrity of the repressor dimer is maintained in TrpR-TN5. Peptide NMR spectroscopy and computer modeling indicate a beta turn as the likely structure for GRGDS peptides. A similar structure may be possible for the SRRGDMS sequence of TrpR-TN5 which is between the D to E helix turn but is not resolved in these preliminary data. The results however, do demonstrate that the SRRGDMS substitution in TrpR can be analyzed by NMR spectroscopy.

Similar types of analyses as described for TrpR-tenascin hybrid fusion proteins can be performed for TrpR-fibronectin peptide or for TrpR-alpha interferon hybrid fusion proteins prepared as described above.

The foregoing specification, including the specific embodiments and examples, is intended to be illustrative of the present invention and is not to be taken as limiting. Numerous other variations and modification can be effected without departing from the true spirit and scope of the present invention.

SEQUENCE LISTING

SEQ ID NO 20

```
GATCCGGAAACGAATATCAACATTGGCACCAGTTACCTGCAATATGTTTATCAGCAGTTT         60

GGCAATAATCGTATTTTCTCCTCAGCAGCTTATAACGCCGGACTAGGGCGGGTGCGAACC         120

TGGCTTGGCAACAGCGCCGGGCGTATCGACGCAGTGGCATTTGTCGAGAGTATTCCATTC         180

TCCGAGACGCGCGGTTATGTGAAGAACGTGCTGGCTTATGACGCTTACTACCGCTATTTC         240

ATGGGGGATAAACCGACGTTGATGAGCGCCACGGAATGGGGACGTCGTTACTGATCCGCA         320

CGTTTATGATATGCTATCGTACTCTTTAGCGAGTACAACCGGGGGAGGCATTTTGCTTCC         360

CCCGCTAACAATGGCGACATATTATGGCCCAACAATCACCCTATTCAGCAGCGATGGCAG         420
                                                  M  A  Q  S  P  Y  S  A  A  M  A

AACAGCGTCACCAGGAGTGGTTACGTTTTGTCGACCTGCTTAAGAATGCCTACCAAAACG          480
 E  Q  R  H  Q  E  W  L  R  F  V  D  L  L  K  N  A  Y  Q  N

ATCTCCATTTACCGTTGTTAAACCTGATGCTGACGCCAGATGAGCGCGAAGCGTTGGGGA          540
 D  L  H  L  P  L  L  N  L  M  L  T  P  D  E  R  E  A  L  G

CTCGCGTGCGTATTGTCGAAGAGCTGTTGCGCGGCGAAATGAGCCAGCGTGAGTTAAAAA          600
 T  R  V  R  I  V  E  E  L  L  R  G  E  M  S  Q  R  E  L  K

ATGAACTCGGCGCAGGCATCGCGACGATTACGCGTGGATCTAACAGCCTGAAAGCCGCGC          660
 N  E  L  G  A  G  I  A  T  I  T  R  G  S  N  S  L  K  A  A

CCGTCGAGCTGCGCCAGTGGCTGGAAGAGGTGTTGCTGAAAAGCGATTGATTTTGTAGGC         720
```

SEQUENCE LISTING

| P | V | E | L | R | Q | W | L | E | E | V - L | L | K | S | D | | |
|---|---|---|---|---|---|---|---|---|---|---|---|---|---|---|---|---|

CTGATAAGACGTGGCGCATCAGGCATCGTGCACCGAATGCCGGATGCGGCGTGAACGCCT 780

TATCCGTCCTACAAATACCCGTAATTTCAATATGTTTGGTAGGCATGATAAGACGCGGCA 840

GCGTCGCATCAGGCGCTTAATACACGGCATTATGAAACGGACTCAGCGCCAGGATCACCG 900

CCTGGTGATAGACGCTGGCGCGAGTGAGTTTCCCGGCGGTAAACACGCCGATCGCCCCTT 980

CCTTACGACCGATCTCATCAATACCGGTATAACGCGACATCACGGGACCAAGCGCCTCAC 1020

CTTCACGCACTTTTTCCAGAGT 1040

What is claimed is:

1. A tryptophan aporepressor containing within its amino acid residue sequence a peptide segment heterologous to said aporepressor, said segment being located on an aqueous solvent-accessible surface of said aporepressor and containing about 3-20 amino acid residues, wherein said peptide segment comprises a ligand binding site.

2. A protein of the formula:

and U is a sequence of amino acid residues represented by the formula:

—AAMAEQRHQEWLRFVDLL-
KNAYQNDLHLPLLNLMLTPDEREA
LGTRVRIVEELLRGEMSQRELKNEL-
GAGIATITRGSNSLKAAP
VELRQWLEEVLLKSK

4. The protein of claim 2 wherein Z is a sequence of amino acid residues represented by the formula (SEQ ID NO 2):

MAQQSPYSAAMAEQRHQEWLRFVDLL-
KNAYQNDLHLPLLNLMLT
PDEREALGTRVRIVEE— and U is a sequence of amino acid residues represented by the formula:

—SQRELKNELGAGIATITRGSNSLKAAP-
VELRQWLEEVLLKSD

5. The protein of claim 2 wherein Z is a sequence of amino acid residues represented by the formula SEQ ID NO 3)

MAQQSPYSAAMAEQRHQEWLRFVDLL-
KNAYQNDLHLPLLNLMLT
PDEREALGTRVRIVEELLRGEM— and U is a sequence of amino acid residues represented by the formula:

—ELGAGIATITRGSNSLKAAPVELRQ-
WLEEVLLKSD

6. The protein of claim 2 wherein Z is a sequence of amino acid residues represented by the formula (SEQ ID NO 4):

MAQQSPYSAAMAEQRHQEWLRFVDLL-
KNAYQNDLHLPLLNLMLT
PDEREALGTRVRIVEELLRGEMSQ-
RELK— and U is a sequence of amino acid residues represented by the formula:

—ATITRGSNSLKAAPVELRQWLEEVLLKSD

7. The protein of claim 2 wherein Z is a sequence of amino acid residues represented by the formula (SEQ ID NO 5):

MAQQSPYSAAMAEQRHQEWLRFVDLL-
KNAYQNDLHLPLLNLMLT
PDEREALGTRVRIVEELLRGEMSQ-
RELKN— and U is a sequence of amino acid residues represented by the formula:

—ITRGSNSLKAAPVELRQWLEEVLLKSD

8. The protein of claim 2 wherein Z is a sequence of amino acid residues represented by the formula (SEQ ID NO 7):

MAQQSPYSAAMAEQRHQEWLRFVDLL-
KNAYQN— and U is a sequence of amino acid residues represented by the formula:

—LHLPLLNLMLTPDEREALGTR-
VRIVEELLRGEMSQRELKN
ELGAGIATITRGSNSLKAAPVELRQ-
WLEEVLLKSD

9. The protein of claim 2 wherein Z is a sequence of amino acid residues represented by the formula (SEQ ID NO 8):

MAQQ— and U is a sequence of amino acid residues represented by the formula:

—SPYSAAMAEQRHQEWLRFVDLL-
KNAYQNDLHLPLLNLMLTPDE
REALGTRVRIVEELLRGEMSQRELKNEL-
GAGIATITRGSNSLKA
APVELRQWLEEVLLKSD

10. The protein of claim 2 wherein Z is a sequence of amino acid residues represented by the formula (SEQ ID NO 9):

MAQQSPYSAAMAEQRHQEWLRFVDLL-
KNAYQ— and U is a sequence of amino acid residues represented by the formula:

—LHLPLLNLMLTPDEREALGTR-
VRIVEELLRGEMSQRELKN
ELGAGIATITRGSNSLKAAPVELRQ-
WLEEVLLKSD

11. The protein of claim 2 wherein Z is a sequence of amino acid residues represented by the formula (SEQ ID NO 10):

MAQQSPYSAAMAEQRHQEWLRFVDLL-
KNAYQNDLHLPLLNLMLT
PDEREALGTRVRIVEELL— and U is a sequence of amino acid residues represented by the formula:

—QRELKNELGAGIATITRGSNSLKAAP-
VELRQWLEEVLLKSD

12. The protein of claim 2 wherein Z is a sequence of amino acid residues represented by the formula (SEQ ID NO 11):

MAQQSPYSAAMAEQRHQEWLRFVDLL-
KNAYQNDLHLPLLNLMLT
PDEREALGTRVRIVEELLRGEMSQ— and U is a sequence of amino acid residues represented by the formula:

—GIATITRGSNSLKAAPVELRQ-
WLEEVLLKSD

13. The protein of claim 2 wherein Z is a sequence of amino acid residues represented by the formula (SEQ ID NO 12):

MAQQSPYSAAMAEQRHQEWLRFVDLL-
KNAYQNDLHLPLLNLMLT
PDEREALGTRVRIVEELLRGEMSQRE— and U is a sequence of amino acid residues represented by the formula:

—ATITRGSNSLKAAPVELRQWLEEVLLKSD

14. The protein of claim 2 wherein Z is a sequence of amino acid residues represented by the formula (SEQ ID NO 14):

MAQQSPYSAAMAEQRHQEWLRFVDLL-
KNAYQNDLHLPLLNLML and U is a sequence of amino acid residues represented by the formula:

—TRVRIVEELLRGEMSQRELKNEL-
GAGIATITRGSNSLKAA
PVELRQWLEEVLLKSD

15. The protein of claim 2 wherein Z is a sequence of amino acid residues represented by the formula (SEQ ID NO 15):

MAQQSPYSAAMAEQRHQEWLRFVDLL-
KNAYQNDLHLPLLNLMLT
PDEREALGTRVRIVEELLRGEMSQR— and U is a sequence of amino acid residues represented by the formula:

—IATITRGSNSLKAAPVELRQ-
WLEEVLLKSD

16. The protein of claim 2 wherein Z is a sequence of amino acid residues represented by the formula (SEQ ID NO 16):
MAQQS— and U is a sequence of amino acid residues represented by the formula:

—AAMAEQRHQEWLRFVDLL-
KNAYQNDLHLPLLNLMLTPDEREA
LGTRVRIVEELLRGEMSQRELKNEL-
GAGIATITRGSNSL
KAAPVELRQWLEEVLLKSD

17. The protein of claim 2 wherein Z is a sequence of amino acid residues represented by the formula (SEQ ID NO 17):

MAQQSPYSAAMAEQRHQEWLRFVDLL-
KNAYQNDLHLPLLNLMLT
PDEREALGTRVRIVEEL— and U is a sequence of amino acid residues represented by the formula:

—QRELKNELGAGIATITRGSNSLKAAP-
VELRQWLEEVLLKSD

18. The protein of claim 2 wherein Z is a sequence of amino acid residues represented by the formula (SEQ ID NO 18):

MAQQSPYSAAMAEQRHQEWLRFVDLL-
KNAYQNDLHLPLLNLMLT
PDEREALGTRVRIVEELLRGEMS— and U is a sequence of amino acid residues represented by the formula:

—ELGAGIATITRGSNSLKAAPVELRQ-
WLEEVLLKSD

19. The protein of claim 2 wherein Z is a sequence of amino acid residues represented by the formula (SEQ ID NO 19):

MAQQSPYSAAMAEQRHQEWLRFVDLL-
KNAYQNDLHLPLLNLMLT
PDEREALGTRVRIVEELLRGEMSQ-
RELKN— and U is a sequence of amino acid residues represented by the formula:

—ATITRGSNSLKAAPVELRQWLEEVLLKSD

* * * * *

SEQUENCE LISTING ( 1 ) GENERAL INFORMATION:

( i i i ) NUMBER OF SEQUENCES: 58

( v i ) CURRENT APPLICATION DATA:
        ( A ) APPLICATION NUMBER: US 07/720,222
        ( B ) FILING DATE: 21-JUN-1991

( 2 ) INFORMATION FOR SEQ ID NO:1:

( i ) SEQUENCE CHARACTERISTICS:
        ( A ) LENGTH: 105 amino acids
        ( B ) TYPE: amino acid
        ( C ) STRANDEDNESS: single
        ( D ) TOPOLOGY: unknown ( i i ) MOLECULE TYPE: protein ( i x ) FEATURE:
        ( A ) NAME/KEY: Peptide
        ( B ) LOCATION: 5
        ( D ) OTHER INFORMATION: /label=PEPTIDE
            / note="Xaa is a peptide segment heterologous to said tryptophan receptor, said peptide segment being 3 to 20 amino acid residues in length."

( x i ) SEQUENCE DESCRIPTION: SEQ ID NO:1:

```
Met Ala Gln Gln Xaa Ala Ala Met Ala Glu Gln Arg His Gln Glu Trp
 1               5                  10                  15

Leu Arg Phe Val Asp Leu Leu Lys Asn Ala Tyr Gln Asn Asp Leu His
            20                  25                  30

Leu Pro Leu Leu Asn Leu Met Leu Thr Pro Asp Glu Arg Glu Ala Leu
        35                  40                  45

Gly Thr Arg Val Arg Ile Val Glu Glu Leu Leu Arg Gly Glu Met Ser
    50                  55                  60

Gln Arg Glu Leu Lys Asn Glu Leu Gly Ala Gly Ile Ala Thr Ile Thr
65                  70                  75                  80

Arg Gly Ser Asn Ser Leu Lys Ala Ala Pro Val Glu Leu Arg Gln Trp
                85                  90                  95

Leu Glu Glu Val Leu Leu Lys Ser Asp
            100                 105
```

( 2 ) INFORMATION FOR SEQ ID NO:2:

( i ) SEQUENCE CHARACTERISTICS:
        ( A ) LENGTH: 103 amino acids
        ( B ) TYPE: amino acid
        ( C ) STRANDEDNESS: single
        ( D ) TOPOLOGY: unknown ( i i ) MOLECULE TYPE: protein ( i x ) FEATURE:
  ( A ) NAME/KEY: Peptide
  ( B ) LOCATION: 61
  ( D ) OTHER INFORMATION: /label=Peptide
    / note="Xaa is a peptide segment being 3 to 20
    amino acid residues in length."

( x i ) SEQUENCE DESCRIPTION: SEQ ID NO:2:

Met Ala Gln Gln Ser Pro Tyr Ser Ala Ala Met Ala Glu Gln Arg His
1               5                   10                  15

Gln Glu Trp Leu Arg Phe Val Asp Leu Leu Lys Asn Ala Tyr Gln Asn
            20              25                  30

Asp Leu His Leu Pro Leu Leu Asn Leu Met Leu Thr Pro Asp Glu Arg
        35              40              45

Glu Ala Leu Gly Thr Arg Val Arg Ile Val Glu Glu Xaa Ser Gln Arg
    50              55              60

Glu Leu Lys Asn Glu Leu Gly Ala Gly Ile Ala Thr Ile Thr Arg Gly
65              70              75              80

Ser Asn Ser Leu Lys Ala Ala Pro Val Glu Leu Arg Gln Trp Leu Glu
            85              90                  95

Glu Val Leu Leu Lys Ser Asp
            100

( 2 ) INFORMATION FOR SEQ ID NO:3:

( i ) SEQUENCE CHARACTERISTICS:
    ( A ) LENGTH: 102 amino acids
    ( B ) TYPE: amino acid
    ( C ) STRANDEDNESS: single
    ( D ) TOPOLOGY: unknown ( i i ) MOLECULE TYPE: protein ( i x ) FEATURE:
    ( A ) NAME/KEY: Peptide
    ( B ) LOCATION: 67
    ( D ) OTHER INFORMATION: /label=Peptide
      / note="Xaa is a peptide segment being 3 to 20
      amino acid residues in length."

( x i ) SEQUENCE DESCRIPTION: SEQ ID NO:3:

Met Ala Gln Gln Ser Pro Tyr Ser Ala Ala Met Ala Glu Gln Arg His
1               5                   10                  15

Gln Glu Trp Leu Arg Phe Val Asp Leu Leu Lys Asn Ala Tyr Gln Asn
            20              25                  30

Asp Leu His Leu Pro Leu Leu Asn Leu Met Leu Thr Pro Asp Glu Arg
        35              40              45

Glu Ala Leu Gly Thr Arg Val Arg Ile Val Glu Glu Leu Leu Arg Gly
    50              55              60

Glu Met Xaa Glu Leu Gly Ala Gly Ile Ala Thr Ile Thr Arg Gly Ser
65              70              75              80

Asn Ser Leu Lys Ala Ala Pro Val Glu Leu Arg Gln Trp Leu Glu Glu
            85              90                  95

Val Leu Leu Lys Ser Asp
            100

( 2 ) INFORMATION FOR SEQ ID NO:4:

( i ) SEQUENCE CHARACTERISTICS:
    ( A ) LENGTH: 102 amino acids
    ( B ) TYPE: amino acid
    ( C ) STRANDEDNESS: single
    ( D ) TOPOLOGY: unknown ( i i ) MOLECULE TYPE: protein (ix) FEATURE:
(A) NAME/KEY: Peptide
(B) LOCATION: 73
(D) OTHER INFORMATION: /label=Peptide
/ note="Xaa is a peptide segment being 3 to 20
amino acid residues in length."

(xi) SEQUENCE DESCRIPTION: SEQ ID NO:4:

```
Met Ala Gln Gln Ser Pro Tyr Ser Ala Ala Met Ala Glu Gln Arg His
1               5                   10                  15
Gln Glu Trp Leu Arg Phe Val Asp Leu Leu Lys Asn Ala Tyr Gln Asn
            20                  25                  30
Asp Leu His Leu Pro Leu Leu Asn Leu Met Leu Thr Pro Asp Glu Arg
        35                  40                  45
Glu Ala Leu Gly Thr Arg Val Arg Ile Val Glu Glu Leu Leu Arg Gly
    50                  55                  60
Glu Met Ser Gln Arg Glu Leu Lys Xaa Ala Thr Ile Thr Arg Gly Ser
65                  70                  75                  80
Asn Ser Leu Lys Ala Ala Pro Val Glu Leu Arg Gln Trp Leu Glu Glu
                85                  90                  95
Val Leu Leu Lys Ser Asp
             100
```

(2) INFORMATION FOR SEQ ID NO:5:

(i) SEQUENCE CHARACTERISTICS:
(A) LENGTH: 101 amino acids
(B) TYPE: amino acid
(C) STRANDEDNESS: single
(D) TOPOLOGY: unknown (ii) MOLECULE TYPE: protein (ix) FEATURE:
(A) NAME/KEY: Peptide
(B) LOCATION: 74
(D) OTHER INFORMATION: /label=Peptide
/ note="Xaa is a peptide segment being 3 to 20
amino acid residues in length."

(xi) SEQUENCE DESCRIPTION: SEQ ID NO:5:

```
Met Ala Gln Gln Ser Pro Tyr Ser Ala Ala Met Ala Glu Gln Arg His
1               5                   10                  15
Gln Glu Trp Leu Arg Phe Val Asp Leu Leu Lys Asn Ala Tyr Gln Asn
            20                  25                  30
Asp Leu His Leu Pro Leu Leu Asn Leu Met Leu Thr Pro Asp Glu Arg
        35                  40                  45
Glu Ala Leu Gly Thr Arg Val Arg Ile Val Glu Glu Leu Leu Arg Gly
    50                  55                  60
Glu Met Ser Gln Arg Glu Leu Lys Asn Xaa Ile Thr Arg Gly Ser Asn
65                  70                  75                  80
Ser Leu Lys Ala Ala Pro Val Glu Leu Arg Gln Trp Leu Glu Glu Val
                85                  90                  95
Leu Leu Lys Ser Asp
             100
```

(2) INFORMATION FOR SEQ ID NO:6:

(i) SEQUENCE CHARACTERISTICS:
(A) LENGTH: 109 amino acids
(B) TYPE: amino acid
(C) STRANDEDNESS: single
(D) TOPOLOGY: unknown (ii) MOLECULE TYPE: protein ( i x ) FEATURE:
    ( A ) NAME/KEY: Peptide
    ( B ) LOCATION: 109
    ( D ) OTHER INFORMATION: /label=Peptide
        / note="Xaa is a peptide segment being 3 to 20
        amino acid residues in length."

( x i ) SEQUENCE DESCRIPTION: SEQ ID NO:6:

```
Met Ala Gln Gln Ser Pro Tyr Ser Ala Ala Met Ala Glu Gln Arg His
1               5                   10                  15

Gln Glu Trp Leu Arg Phe Val Asp Leu Leu Lys Asn Ala Tyr Gln Asn
                20                  25                  30

Asp Leu His Leu Pro Leu Leu Asn Leu Met Leu Thr Pro Asp Glu Arg
            35                  40                  45

Glu Ala Leu Gly Thr Arg Val Arg Ile Val Glu Glu Leu Leu Arg Gly
        50                  55                  60

Glu Met Ser Gln Arg Glu Leu Lys Asn Glu Leu Gly Ala Gly Ile Ala
65                  70                  75                  80

Thr Ile Thr Arg Gly Ser Asn Ser Leu Lys Ala Ala Pro Val Glu Leu
                85                  90                  95

Arg Gln Trp Leu Glu Glu Val Leu Leu Lys Ser Asp Xaa
                100                 105
```

( 2 ) INFORMATION FOR SEQ ID NO:7:

( i ) SEQUENCE CHARACTERISTICS:
        ( A ) LENGTH: 108 amino acids
        ( B ) TYPE: amino acid
        ( C ) STRANDEDNESS: single
        ( D ) TOPOLOGY: unknown ( i i ) MOLECULE TYPE: protein ( i x ) FEATURE:
        ( A ) NAME/KEY: Peptide
        ( B ) LOCATION: 33
        ( D ) OTHER INFORMATION: /label=Peptide
            / note="Xaa is a peptide segment being 3 to 20
            amino acid residues in length."

( x i ) SEQUENCE DESCRIPTION: SEQ ID NO:7:

```
Met Ala Gln Gln Ser Pro Tyr Ser Ala Ala Met Ala Glu Gln Arg His
1               5                   10                  15

Gln Glu Trp Leu Arg Phe Val Asp Leu Leu Lys Asn Ala Tyr Gln Asn
                20                  25                  30

Xaa Leu His Leu Pro Leu Leu Asn Leu Met Leu Thr Pro Asp Glu Arg
            35                  40                  45

Glu Ala Leu Gly Thr Arg Val Arg Ile Val Glu Glu Leu Leu Arg Gly
        50                  55                  60

Glu Met Ser Gln Arg Glu Leu Lys Asn Glu Leu Gly Ala Gly Ile Ala
65                  70                  75                  80

Thr Ile Thr Arg Gly Ser Asn Ser Leu Lys Ala Ala Pro Val Glu Leu
                85                  90                  95

Arg Gln Trp Leu Glu Glu Val Leu Leu Lys Ser Asp
                100                 105
```

( 2 ) INFORMATION FOR SEQ ID NO:8:

( i ) SEQUENCE CHARACTERISTICS:
        ( A ) LENGTH: 109 amino acids
        ( B ) TYPE: amino acid
        ( C ) STRANDEDNESS: single
        ( D ) TOPOLOGY: unknown ( i i ) MOLECULE TYPE: protein ( i x ) FEATURE:
   ( A ) NAME/KEY: Peptide
   ( B ) LOCATION: 5
   ( D ) OTHER INFORMATION: /label=Peptide
       / note="Xaa is a peptide segment being 3 to 20
       amino acid residues in length."

( x i ) SEQUENCE DESCRIPTION: SEQ ID NO:8:

```
Met Ala Gln Gln Xaa Ser Pro Tyr Ser Ala Ala Met Ala Glu Gln Arg
1               5                   10                  15

His Gln Glu Trp Leu Arg Phe Val Asp Leu Leu Lys Asn Ala Tyr Gln
            20                  25                  30

Asn Asp Leu His Leu Pro Leu Leu Asn Leu Met Leu Thr Pro Asp Glu
            35                  40                  45

Arg Glu Ala Leu Gly Thr Arg Val Arg Ile Val Glu Glu Leu Leu Arg
    50                  55                  60

Gly Glu Met Ser Gln Arg Glu Leu Lys Asn Glu Leu Gly Ala Gly Ile
65                      70                  75                  80

Ala Thr Ile Thr Arg Gly Ser Asn Ser Leu Lys Ala Ala Pro Val Glu
                85                  90                  95

Leu Arg Gln Trp Leu Glu Glu Val Leu Leu Lys Ser Asp
            100                 105
```

( 2 ) INFORMATION FOR SEQ ID NO:9:

( i ) SEQUENCE CHARACTERISTICS:
       ( A ) LENGTH: 107 amino acids
       ( B ) TYPE: amino acid
       ( C ) STRANDEDNESS: single
       ( D ) TOPOLOGY: unknown ( i i ) MOLECULE TYPE: protein ( i x ) FEATURE:
   ( A ) NAME/KEY: Peptide
   ( B ) LOCATION: 32
   ( D ) OTHER INFORMATION: /label=Peptide
       / note="Xaa is a peptide segment being 3 to 20
       amino acid residues in length."

( x i ) SEQUENCE DESCRIPTION: SEQ ID NO:9:

```
Met Ala Gln Gln Ser Pro Tyr Ser Ala Ala Met Ala Glu Gln Arg His
1               5                   10                  15

Gln Glu Trp Leu Arg Phe Val Asp Leu Leu Lys Asn Ala Tyr Gln Xaa
            20                  25                  30

Leu His Leu Pro Leu Leu Asn Leu Met Leu Thr Pro Asp Glu Arg Glu
            35                  40                  45

Ala Leu Gly Thr Arg Val Arg Ile Val Glu Glu Leu Leu Arg Gly Glu
    50                  55                  60

Met Ser Gln Arg Glu Leu Lys Asn Glu Leu Gly Ala Gly Ile Ala Thr
65                      70                  75                  80

Ile Thr Arg Gly Ser Asn Ser Leu Lys Ala Ala Pro Val Glu Leu Arg
                85                  90                  95

Gln Trp Leu Glu Glu Val Leu Leu Lys Ser Asp
            100                 105
```

( 2 ) INFORMATION FOR SEQ ID NO:10:

( i ) SEQUENCE CHARACTERISTICS:
       ( A ) LENGTH: 104 amino acids
       ( B ) TYPE: amino acid
       ( C ) STRANDEDNESS: single
       ( D ) TOPOLOGY: unknown ( i i ) MOLECULE TYPE: protein ( i x ) FEATURE:
  ( A ) NAME/KEY: Peptide
  ( B ) LOCATION: 63
  ( D ) OTHER INFORMATION: /label=Peptide
    / note="Xaa is a peptide segment being 3 to 20
    amino acid residues in length."

( x i ) SEQUENCE DESCRIPTION: SEQ ID NO:10:

```
Met Ala Gln Gln Ser Pro Tyr Ser Ala Ala Met Ala Glu Gln Arg His
1               5                   10                  15
Gln Glu Trp Leu Arg Phe Val Asp Leu Leu Lys Asn Ala Tyr Gln Asn
            20                  25                  30
Asp Leu His Leu Pro Leu Leu Asn Leu Met Leu Thr Pro Asp Glu Arg
        35                  40                  45
Glu Ala Leu Gly Thr Arg Val Arg Ile Val Glu Glu Leu Leu Xaa Gln
    50                  55                  60
Arg Glu Leu Lys Asn Glu Leu Gly Ala Gly Ile Ala Thr Ile Thr Arg
65                  70                  75                  80
Gly Ser Asn Ser Leu Lys Ala Ala Pro Val Glu Leu Arg Gln Trp Leu
                85                  90                  95
Glu Glu Val Leu Leu Lys Ser Asp
                100
```

( 2 ) INFORMATION FOR SEQ ID NO:11:

( i ) SEQUENCE CHARACTERISTICS:
    ( A ) LENGTH: 100 amino acids
    ( B ) TYPE: amino acid
    ( C ) STRANDEDNESS: single
    ( D ) TOPOLOGY: unknown ( i i ) MOLECULE TYPE: protein ( i x ) FEATURE:
    ( A ) NAME/KEY: Peptide
    ( B ) LOCATION: 69
    ( D ) OTHER INFORMATION: /label=Peptide
      / note="Xaa is a peptide segment being 3 to 20
      amino acid residues in length."

( x i ) SEQUENCE DESCRIPTION: SEQ ID NO:11:

```
Met Ala Gln Gln Ser Pro Tyr Ser Ala Ala Met Ala Glu Gln Arg His
1               5                   10                  15
Gln Glu Trp Leu Arg Phe Val Asp Leu Leu Lys Asn Ala Tyr Gln Asn
            20                  25                  30
Asp Leu His Leu Pro Leu Leu Asn Leu Met Leu Thr Pro Asp Glu Arg
        35                  40                  45
Glu Ala Leu Gly Thr Arg Val Arg Ile Val Glu Glu Leu Leu Arg Gly
    50                  55                  60
Glu Met Ser Gln Xaa Gly Ile Ala Thr Ile Thr Arg Gly Ser Asn Ser
65              70                  75                  80
Leu Lys Ala Ala Pro Val Glu Leu Arg Gln Trp Leu Glu Glu Val Leu
                85                  90                  95
Leu Lys Ser Asp
            100
```

( 2 ) INFORMATION FOR SEQ ID NO:12:

( i ) SEQUENCE CHARACTERISTICS:
    ( A ) LENGTH: 100 amino acids
    ( B ) TYPE: amino acid
    ( C ) STRANDEDNESS: single
    ( D ) TOPOLOGY: unknown ( i i ) MOLECULE TYPE: protein ( i x ) FEATURE:
    ( A ) NAME/KEY: Peptide
    ( B ) LOCATION: 71
    ( D ) OTHER INFORMATION: /label=Peptide
        / note="Xaa is a peptide segment being 3 to 20
        amino acid residues in length."

( x i ) SEQUENCE DESCRIPTION: SEQ ID NO:12:

| Met | Ala | Gln | Gln | Ser | Pro | Tyr | Ser | Ala | Ala | Met | Ala | Glu | Gln | Arg | His |
|---|---|---|---|---|---|---|---|---|---|---|---|---|---|---|---|
| 1 | | | | 5 | | | | | 10 | | | | | 15 | |

| Gln | Glu | Trp | Leu | Arg | Phe | Val | Asp | Leu | Leu | Lys | Asn | Ala | Tyr | Gln | Asn |
|---|---|---|---|---|---|---|---|---|---|---|---|---|---|---|---|
| | | | 20 | | | | | 25 | | | | | 30 | | |

| Asp | Leu | His | Leu | Pro | Leu | Leu | Asn | Leu | Met | Leu | Thr | Pro | Asp | Glu | Arg |
|---|---|---|---|---|---|---|---|---|---|---|---|---|---|---|---|
| | | 35 | | | | | 40 | | | | | 45 | | | |

| Glu | Ala | Leu | Gly | Thr | Arg | Val | Arg | Ile | Val | Glu | Glu | Leu | Leu | Arg | Gly |
|---|---|---|---|---|---|---|---|---|---|---|---|---|---|---|---|
| | 50 | | | | | 55 | | | | | 60 | | | | |

| Glu | Met | Ser | Gln | Arg | Glu | Xaa | Ala | Thr | Ile | Thr | Arg | Gly | Ser | Asn | Ser |
|---|---|---|---|---|---|---|---|---|---|---|---|---|---|---|---|
| 65 | | | | | 70 | | | | | 75 | | | | | 80 |

| Leu | Lys | Ala | Ala | Pro | Val | Glu | Leu | Arg | Gln | Trp | Leu | Glu | Glu | Val | Leu |
|---|---|---|---|---|---|---|---|---|---|---|---|---|---|---|---|
| | | | | 85 | | | | | 90 | | | | | 95 | |

| Leu | Lys | Ser | Asp |
|---|---|---|---|
| | | | 100 |

( 2 ) INFORMATION FOR SEQ ID NO:13:

( i ) SEQUENCE CHARACTERISTICS:
    ( A ) LENGTH: 106 amino acids
    ( B ) TYPE: amino acid
    ( C ) STRANDEDNESS: single
    ( D ) TOPOLOGY: unknown ( i i ) MOLECULE TYPE: protein ( i x ) FEATURE:
    ( A ) NAME/KEY: Peptide
    ( B ) LOCATION: 106
    ( D ) OTHER INFORMATION: /label=Peptide
        / note="Xaa is a peptide segment being 3 to 20
        amino acid residues in length."

( x i ) SEQUENCE DESCRIPTION: SEQ ID NO:13:

| Met | Ala | Gln | Gln | Ser | Pro | Tyr | Ser | Ala | Ala | Met | Ala | Glu | Gln | Arg | His |
|---|---|---|---|---|---|---|---|---|---|---|---|---|---|---|---|
| 1 | | | | 5 | | | | | 10 | | | | | 15 | |

| Gln | Glu | Trp | Leu | Arg | Phe | Val | Asp | Leu | Leu | Lys | Asn | Ala | Tyr | Gln | Asn |
|---|---|---|---|---|---|---|---|---|---|---|---|---|---|---|---|
| | | | 20 | | | | | 25 | | | | | 30 | | |

| Asp | Leu | His | Leu | Pro | Leu | Leu | Asn | Leu | Met | Leu | Thr | Pro | Asp | Glu | Arg |
|---|---|---|---|---|---|---|---|---|---|---|---|---|---|---|---|
| | | 35 | | | | | 40 | | | | | 45 | | | |

| Glu | Ala | Leu | Gly | Thr | Arg | Val | Arg | Ile | Val | Glu | Glu | Leu | Leu | Arg | Gly |
|---|---|---|---|---|---|---|---|---|---|---|---|---|---|---|---|
| | 50 | | | | | 55 | | | | | 60 | | | | |

| Glu | Met | Ser | Gln | Arg | Glu | Leu | Lys | Asn | Glu | Leu | Gly | Ala | Gly | Ile | Ala |
|---|---|---|---|---|---|---|---|---|---|---|---|---|---|---|---|
| 65 | | | | | 70 | | | | | 75 | | | | | 80 |

| Thr | Ile | Thr | Arg | Gly | Ser | Asn | Ser | Leu | Lys | Ala | Ala | Pro | Val | Glu | Leu |
|---|---|---|---|---|---|---|---|---|---|---|---|---|---|---|---|
| | | | | 85 | | | | | 90 | | | | | 95 | |

| Arg | Gln | Trp | Leu | Glu | Glu | Val | Leu | Leu | Xaa |
|---|---|---|---|---|---|---|---|---|---|
| | | | 100 | | | | | 105 | |

( 2 ) INFORMATION FOR SEQ ID NO:14:

( i ) SEQUENCE CHARACTERISTICS:
    ( A ) LENGTH: 100 amino acids
    ( B ) TYPE: amino acid
    ( C ) STRANDEDNESS: single
    ( D ) TOPOLOGY: unknown ( i i ) MOLECULE TYPE: protein ( i x ) FEATURE:
        ( A ) NAME/KEY: Peptide
        ( B ) LOCATION: 44
        ( D ) OTHER INFORMATION: /label=Peptide
                / note="Xaa is a peptide segment being 3 to 20
                amino acid residues in length."

( x i ) SEQUENCE DESCRIPTION: SEQ ID NO:14:

```
Met Ala Gln Gln Ser Pro Tyr Ser Ala Ala Met Ala Glu Gln Arg His
1               5                   10                  15

Gln Glu Trp Leu Arg Phe Val Asp Leu Leu Lys Asn Ala Tyr Gln Asn
            20                  25                  30

Asp Leu His Leu Pro Leu Leu Asn Leu Met Leu Xaa Thr Arg Val Arg
        35                  40                  45

Ile Val Glu Glu Leu Leu Arg Gly Glu Met Ser Gln Arg Glu Leu Lys
    50              55                  60

Asn Glu Leu Gly Ala Gly Ile Ala Thr Ile Thr Arg Gly Ser Asn Ser
65              70                  75                      80

Leu Lys Ala Ala Pro Val Glu Leu Arg Gln Trp Leu Glu Glu Val Leu
                85                  90                  95

Leu Lys Ser Asp
            100
```

( 2 ) INFORMATION FOR SEQ ID NO:15:

( i ) SEQUENCE CHARACTERISTICS:
        ( A ) LENGTH: 100 amino acids
        ( B ) TYPE: amino acid
        ( C ) STRANDEDNESS: single
        ( D ) TOPOLOGY: unknown ( i i ) MOLECULE TYPE: protein ( i x ) FEATURE:
        ( A ) NAME/KEY: Peptide
        ( B ) LOCATION: 70
        ( D ) OTHER INFORMATION: /label=Peptide
                / note="Xaa is a peptide segment being 3 to 20
                amino acid residues in length."

( x i ) SEQUENCE DESCRIPTION: SEQ ID NO:15:

```
Met Ala Gln Gln Ser Pro Tyr Ser Ala Ala Met Ala Glu Gln Arg His
1               5                   10                  15

Gln Glu Trp Leu Arg Phe Val Asp Leu Leu Lys Asn Ala Tyr Gln Asn
            20                  25                  30

Asp Leu His Leu Pro Leu Leu Asn Leu Met Leu Thr Pro Asp Glu Arg
        35                  40                  45

Glu Ala Leu Gly Thr Arg Val Arg Ile Val Glu Glu Leu Leu Arg Gly
    50              55                  60

Glu Met Ser Gln Arg Xaa Ile Ala Thr Ile Thr Arg Gly Ser Asn Ser
65              70                  75                      80

Leu Lys Ala Ala Pro Val Glu Leu Arg Gln Trp Leu Glu Glu Val Leu
                85                  90                  95

Leu Lys Ser Asp
            100
```

( 2 ) INFORMATION FOR SEQ ID NO:16:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: unknown ( i i ) MOLECULE TYPE: protein (ix) FEATURE:
    (A) NAME/KEY: Peptide
    (B) LOCATION: 6
    (D) OTHER INFORMATION: /label=Peptide
        / note="Xaa is a peptide segment being 3 to 20
        amino acid residues in length."

(xi) SEQUENCE DESCRIPTION: SEQ ID NO:16:

| Met | Ala | Gln | Gln | Ser | Xaa | Ala | Ala | Met | Ala | Glu | Gln | Arg | His | Gln | Glu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Trp | Leu | Arg | Phe | Val | Asp | Leu | Leu | Lys | Asn | Ala | Tyr | Gln | Asn | Asp | Leu |
|     |     |     | 20  |     |     |     |     | 25  |     |     |     |     | 30  |     |     |
| His | Leu | Pro | Leu | Leu | Asn | Leu | Met | Leu | Thr | Pro | Asp | Glu | Arg | Glu | Ala |
|     |     | 35  |     |     |     |     | 40  |     |     |     |     | 45  |     |     |     |
| Leu | Gly | Thr | Arg | Val | Arg | Ile | Val | Glu | Glu | Leu | Leu | Arg | Gly | Glu | Met |
|     | 50  |     |     |     |     | 55  |     |     |     |     | 60  |     |     |     |     |
| Ser | Gln | Arg | Glu | Leu | Lys | Asn | Glu | Leu | Gly | Ala | Gly | Ile | Ala | Thr | Ile |
| 65  |     |     |     |     | 70  |     |     |     |     | 75  |     |     |     |     | 80  |
| Thr | Arg | Gly | Ser | Asn | Ser | Leu | Lys | Ala | Ala | Pro | Val | Glu | Leu | Arg | Gln |
|     |     |     |     | 85  |     |     |     |     | 90  |     |     |     |     | 95  |     |
| Trp | Leu | Glu | Glu | Val | Leu | Leu | Lys | Ser | Asp |
|     |     |     | 100 |     |     |     |     | 105 |     |

(2) INFORMATION FOR SEQ ID NO:17:

(i) SEQUENCE CHARACTERISTICS:
        (A) LENGTH: 103 amino acids
        (B) TYPE: amino acid
        (C) STRANDEDNESS: single
        (D) TOPOLOGY: unknown (ii) MOLECULE TYPE: protein (ix) FEATURE:
        (A) NAME/KEY: Peptide
        (B) LOCATION: 62
        (D) OTHER INFORMATION: /label=Peptide
            / note="Xaa is a peptide segment being 3 to 20
            amino acid residues in length."

(xi) SEQUENCE DESCRIPTION: SEQ ID NO:17:

| Met | Ala | Gln | Gln | Ser | Pro | Tyr | Ser | Ala | Ala | Met | Ala | Glu | Gln | Arg | His |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Gln | Glu | Trp | Leu | Arg | Phe | Val | Asp | Leu | Leu | Lys | Asn | Ala | Tyr | Gln | Asn |
|     |     |     | 20  |     |     |     |     | 25  |     |     |     |     | 30  |     |     |
| Asp | Leu | His | Leu | Pro | Leu | Leu | Asn | Leu | Met | Leu | Thr | Pro | Asp | Glu | Arg |
|     |     |     | 35  |     |     |     |     | 40  |     |     |     |     | 45  |     |     |
| Glu | Ala | Leu | Gly | Thr | Arg | Val | Arg | Ile | Val | Glu | Glu | Leu | Xaa | Gln | Arg |
|     | 50  |     |     |     |     | 55  |     |     |     |     | 60  |     |     |     |     |
| Glu | Leu | Lys | Asn | Glu | Leu | Gly | Ala | Gly | Ile | Ala | Thr | Ile | Thr | Arg | Gly |
| 65  |     |     |     |     | 70  |     |     |     |     | 75  |     |     |     |     | 80  |
| Ser | Asn | Ser | Leu | Lys | Ala | Ala | Pro | Val | Glu | Leu | Arg | Gln | Trp | Leu | Glu |
|     |     |     |     | 85  |     |     |     |     | 90  |     |     |     |     | 95  |     |
| Glu | Val | Leu | Leu | Lys | Ser | Asp |
|     |     |     | 100 |     |     |     |

(2) INFORMATION FOR SEQ ID NO:18:

(i) SEQUENCE CHARACTERISTICS:
        (A) LENGTH: 103 amino acids
        (B) TYPE: amino acid
        (C) STRANDEDNESS: single
        (D) TOPOLOGY: unknown (ii) MOLECULE TYPE: protein ( i x ) FEATURE:
  ( A ) NAME/KEY: Peptide
  ( B ) LOCATION: 68
  ( D ) OTHER INFORMATION: /label=Peptide
    / note="Xaa is a peptide segment being 3 to 20
    amino acid residues in length."

( x i ) SEQUENCE DESCRIPTION: SEQ ID NO:18:

```
Met Ala Gln Gln Ser Pro Tyr Ser Ala Ala Met Ala Glu Gln Arg His
 1               5                  10                  15
Gln Glu Trp Leu Arg Phe Val Asp Leu Leu Lys Asn Ala Tyr Gln Asn
            20                  25                  30
Asp Leu His Leu Pro Leu Leu Asn Leu Met Leu Thr Pro Asp Glu Arg
            35                  40                  45
Glu Ala Leu Gly Thr Arg Val Arg Ile Val Glu Glu Leu Leu Arg Gly
     50                  55                  60
Glu Met Ser Xaa Glu Leu Gly Ala Gly Ile Ala Thr Ile Thr Arg Gly
 65                  70                  75                  80
Ser Asn Ser Leu Lys Ala Ala Pro Val Glu Leu Arg Gln Trp Leu Glu
                85                  90                  95
Glu Val Leu Leu Lys Ser Asp
                100
```

( 2 ) INFORMATION FOR SEQ ID NO:19:

( i ) SEQUENCE CHARACTERISTICS:
    ( A ) LENGTH: 103 amino acids
    ( B ) TYPE: amino acid
    ( C ) STRANDEDNESS: single
    ( D ) TOPOLOGY: unknown ( i i ) MOLECULE TYPE: protein ( i x ) FEATURE:
    ( A ) NAME/KEY: Peptide
    ( B ) LOCATION: 74
    ( D ) OTHER INFORMATION: /label=Peptide
      / note="Xaa is a peptide segment being 3 to 20
      amino acid residues in length."

( x i ) SEQUENCE DESCRIPTION: SEQ ID NO:19:

```
Met Ala Gln Gln Ser Pro Tyr Ser Ala Ala Met Ala Glu Gln Arg His
 1               5                  10                  15
Gln Glu Trp Leu Arg Phe Val Asp Leu Leu Lys Asn Ala Tyr Gln Asn
            20                  25                  30
Asp Leu His Leu Pro Leu Leu Asn Leu Met Leu Thr Pro Asp Glu Arg
            35                  40                  45
Glu Ala Leu Gly Thr Arg Val Arg Ile Val Glu Glu Leu Leu Arg Gly
     50                  55                  60
Glu Met Ser Gln Arg Glu Leu Lys Asn Xaa Ala Thr Ile Thr Arg Gly
 65                  70                  75                  80
Ser Asn Ser Leu Lys Ala Ala Pro Val Glu Leu Arg Gln Trp Leu Glu
                85                  90                  95
Glu Val Leu Leu Lys Ser Asp
                100
```

( 2 ) INFORMATION FOR SEQ ID NO:20:

( i ) SEQUENCE CHARACTERISTICS:
    ( A ) LENGTH: 1042 base pairs
    ( B ) TYPE: nucleic acid
    ( C ) STRANDEDNESS: double
    ( D ) TOPOLOGY: unknown ( i i ) MOLECULE TYPE: DNA (genomic)

( i x ) FEATURE:
  ( A ) NAME/KEY: CDS
  ( B ) LOCATION: 384..707
  ( C ) IDENTIFICATION METHOD: experimental
  ( D ) OTHER INFORMATION: /product="E. coli tryptophan aporepressor"
    / evidence=EXPERIMENTAL
    / standardname="tryptophan aporepressor"

( x i ) SEQUENCE DESCRIPTION: SEQ ID NO:20:

| | | | | |
|---|---|---|---|---|
| GATCCGGAAA | CGAATATCAA | CATTGGCACC | AGTTACCTGC | AATATGTTTA TCAGCAGTTT | 60 |
| GGCAATAATC | GTATTTTCTC | CTCAGCAGCT | TATAACGCCG | GACTAGGGCG GGTGCGAACC | 120 |
| TGGCTTGGCA | ACAGCGCCGG | GCGTATCGAC | GCAGTGGCAT | TTGTCGAGAG TATTCCATTC | 180 |
| TCCGAGACGC | GCGGTTATGT | GAAGAACGTG | CTGGCTTATG | ACGCTTACTA CCGCTATTTC | 240 |
| ATGGGGGATA | AACCGACGTT | GATGAGCGCC | ACGGAATGGG | GACGTCGTTA CTGATCCGCA | 300 |
| CGTTTATGAT | ATGCTATCGT | ACTCTTTAGC | GAGTACAACC | GGGGGAGGCA TTTTGCTTCC | 360 |
| CCCGCTAACA | ATGGCGACAT | ATT ATG GCC CAA CAA TCA CCC TAT TCA GCA | | | 410 |
| | | Met Ala Gln Gln Ser Pro Tyr Ser Ala | | |
| | | 1 5 | | |

```
GCG ATG GCA GAA CAG CGT CAC CAG GAG TGG TTA CGT TTT GTC GAC CTG      458
Ala Met Ala Glu Gln Arg His Gln Glu Trp Leu Arg Phe Val Asp Leu
 10          15                  20                  25

CTT AAG AAT GCC TAC CAA AAC GAT CTC CAT TTA CCG TTG TTA AAC CTG      506
Leu Lys Asn Ala Tyr Gln Asn Asp Leu His Leu Pro Leu Leu Asn Leu
             30                  35                  40

ATG CTG ACG CCA GAT GAG CGC GAA GCG TTG GGG ACT CGC GTG CGT ATT      554
Met Leu Thr Pro Asp Glu Arg Glu Ala Leu Gly Thr Arg Val Arg Ile
                 45                  50                  55

GTC GAA GAG CTG TTG CGC GGC GAA ATG AGC CAG CGT GAG TTA AAA AAT      602
Val Glu Glu Leu Leu Arg Gly Glu Met Ser Gln Arg Glu Leu Lys Asn
             60                  65                  70

GAA CTC GGC GCA GGC ATC GCG ACG ATT ACG CGT GGA TCT AAC AGC CTG      650
Glu Leu Gly Ala Gly Ile Ala Thr Ile Thr Arg Gly Ser Asn Ser Leu
     75                  80                  85

AAA GCC GCG CCC GTC GAG CTG CGC CAG TGG CTG GAA GAG GTG TTG CTG      698
Lys Ala Ala Pro Val Glu Leu Arg Gln Trp Leu Glu Glu Val Leu Leu
 90                  95                  100                 105

AAA AGC GAT TGATTTTGTA GGCCTGATAA GACGTGGCGC ATCAGGCATC              747
Lys Ser Asp
```

| | | | | |
|---|---|---|---|---|
| GTGCACCGAA | TGCCGGATGC | GGCGTGAACG | CCTTATCCGT | CCTACAAATA CCCGTAATTT | 807 |
| CAATATGTTT | GGTAGGCATG | ATAAGACGCG | GCAGCGTCGC | ATCAGGCGCT TAATACACGG | 867 |
| CATTATGAAA | CGGACTCAGC | GCCAGGATCA | CCGCCTGGTG | ATAGACGCTG GCGCGAGTGA | 927 |
| GTTTCCCGGC | GGTAAACACG | CCGATCGCCC | CTTCCTTACG | ACCGATCTCA TCAATACCGG | 987 |
| TATAACGCGA | CATCACGGGA | CCAAGCGCCT | CACCTTCACG | CACTTTTTCC AGAGT | 1042 |

( 2 ) INFORMATION FOR SEQ ID NO:21:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:21:

Ser Arg Arg Gly Asp Met Ser
     1               5

( 2 ) INFORMATION FOR SEQ ID NO:22:

( i ) SEQUENCE CHARACTERISTICS:
        ( A ) LENGTH: 38 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:22:

CCCAACAATC ACGCCGCGGA GACATGTCAG CAGCGATG                                     3 8

( 2 ) INFORMATION FOR SEQ ID NO:23:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:23:

ATTGTCGAAG AGTCACGCCG CGGAGACATG AGCCAGCGT                                    3 9

( 2 ) INFORMATION FOR SEQ ID NO:24:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:24:

GAAGAGCTGT TGTCACGCCG CGGAGACATG AGCCAGCGT                                    3 9

( 2 ) INFORMATION FOR SEQ ID NO:25:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:25:

GCGAAATGAG CCGCCGCGGA GACATGTCTG AACTCGGCGC                                   4 0

( 2 ) INFORMATION FOR SEQ ID NO:26:

( i ) SEQUENCE CHARACTERISTICS:
        ( A ) LENGTH: 44 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:26:

CGTGAGTTAA AATCACGCCG CGGAGACATG TCCGCGACGA TTAC                              4 4

( 2 ) INFORMATION FOR SEQ ID NO:27:

( i ) SEQUENCE CHARACTERISTICS:
        ( A ) LENGTH: 45 base pairs
        ( B ) TYPE: nucleic acid
        ( C ) STRANDEDNESS: double ( D ) TOPOLOGY: linear ( i i ) MOLECULE TYPE: DNA (genomic)

( x i ) SEQUENCE DESCRIPTION: SEQ ID NO:27:

TTAAAAAATG AATCACGCCG CGGAGACATG AGCATTACGG CTGGA 45

( 2 ) INFORMATION FOR SEQ ID NO:28:

( i ) SEQUENCE CHARACTERISTICS:
        ( A ) LENGTH: 41 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:28:

TTGCTGAAAA GCCGCCGCGG AGACATGTCT TGATTTTGTA G 41

( 2 ) INFORMATION FOR SEQ ID NO:29:

( i ) SEQUENCE CHARACTERISTICS:
        ( A ) LENGTH: 42 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:29:

CCAAAACGAT TCACGCCGCG GAGACATGTC TCTCCATTTA CC 42

( 2 ) INFORMATION FOR SEQ ID NO:30:

( i ) SEQUENCE CHARACTERISTICS:
        ( A ) LENGTH: 43 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:30:

GGCCCAACAA TCCGGACGTG GAGACAGGCC TGCAGCGATG GCA 43

( 2 ) INFORMATION FOR SEQ ID NO:31:

( i ) SEQUENCE CHARACTERISTICS:
        ( A ) LENGTH: 42 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:31:

GTCGAAGAGC TCGGACGTGG AGACAGGCCT CAGCGTGAGT TA 42

( 2 ) INFORMATION FOR SEQ ID NO:32:

( i ) SEQUENCE CHARACTERISTICS:
        ( A ) LENGTH: 45 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:32:

GAAGAGCTGT TGTCAGGACG TGGAGACAGG CCTCAGCGTG AGTTA 45

( 2 ) INFORMATION FOR SEQ ID NO:33:

( i ) SEQUENCE CHARACTERISTICS:
        ( A ) LENGTH: 42 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:33:

GGCGAAATGA GCGGACGTGG AGACAGGCCT GAACTCGGCG CA          42

( 2 ) INFORMATION FOR SEQ ID NO:34:

( i ) SEQUENCE CHARACTERISTICS:
        ( A ) LENGTH: 42 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:34:

GAGTTAAAAA ATGGACGTGG AGACAGGCCT GCGACGATTA CG          42

( 2 ) INFORMATION FOR SEQ ID NO:35:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:35:

AATGAACTCG GACGTGGAGA CAGGCCTATT ACGGCTGGA            39

( 2 ) INFORMATION FOR SEQ ID NO:36:

( i ) SEQUENCE CHARACTERISTICS:
        ( A ) LENGTH: 42 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:36:

TTGCTGAAAA GCGGACGTGG AGACAGGCCT TGATTTTGTA GG          42

( 2 ) INFORMATION FOR SEQ ID NO:37:

( i ) SEQUENCE CHARACTERISTICS:
        ( A ) LENGTH: 44 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:37:

TACCAAAACG ATTCAGGACG TGGAGACAGG CCTCTCCATT TACC        44

( 2 ) INFORMATION FOR SEQ ID NO:38:

( i ) SEQUENCE CHARACTERISTICS:
        ( A ) LENGTH: 47 base pairs
        ( B ) TYPE: nucleic acid (C) STRANDEDNESS: double
(D) TOPOLOGY: linear (ii) MOLECULE TYPE: DNA (genomic)

(xi) SEQUENCE DESCRIPTION: SEQ ID NO:38:

ATGGCCCAAC AGCTGAACGA TTTCGAAGCT TGTGTATCAC CCTATTC 47

(2) INFORMATION FOR SEQ ID NO:39:

(i) SEQUENCE CHARACTERISTICS:
        (A) LENGTH: 49 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:39:

GAATGCCTAC CAGCTGAACG ATTTCGAAGC TTGTGTACTC CATTTACCG 49

(2) INFORMATION FOR SEQ ID NO:40:

(i) SEQUENCE CHARACTERISTICS:
        (A) LENGTH: 49 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:40:

AAGAGCTGTT GCAGCTGAAC GATTTCGAAG CTTGTGTCCA GCGTGAGTT 49

(2) INFORMATION FOR SEQ ID NO:41:

(i) SEQUENCE CHARACTERISTICS:
        (A) LENGTH: 48 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:41:

GAAATGAGCC AGCAGCTGAA CGATTTCGAA GCTTGTGTAG GCATCGCG 48

(2) INFORMATION FOR SEQ ID NO:42:

(i) SEQUENCE CHARACTERISTICS:
        (A) LENGTH: 47 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:42:

GCCAGCGTGA GCAGCTGAAC GATTCGAAG CTTGTGTCGC GACGATT 47

(2) INFORMATION FOR SEQ ID NO:43:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:43:

GAGGTGTTGC TGCAGCTGAA CGATTTCGAA GCTTGTGTTT GATTTTGTAG     50

( 2 ) INFORMATION FOR SEQ ID NO:44:

( i ) SEQUENCE CHARACTERISTICS:
        ( A ) LENGTH: 49 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:44:

AACCTGATGC TGCAGCTGAA CGATTTCGAA GCTTGTGTGA CTCGCGTGC     49

( 2 ) INFORMATION FOR SEQ ID NO:45:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:45:

ATGAGCCAGC GTCAGCTGAA CGATTTCGAA GCTTGTGTCA TCGCGACG     48

( 2 ) INFORMATION FOR SEQ ID NO:46:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:46:

Gly Arg Gly Asp Ser Pro
1               5

( 2 ) INFORMATION FOR SEQ ID NO:47:

( i ) SEQUENCE CHARACTERISTICS:
        ( A ) LENGTH: 9 amino acids
        ( B ) TYPE: amino acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:47:

Gln Leu Asn Asp Leu Glu Ala Cys Val
1               5

( 2 ) INFORMATION FOR SEQ ID NO:48:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:48:

AATATGGCCC AATGCTCACG CCGCGGAGGC ATGTCATGCG CAATGGCA     48

( 2 ) INFORMATION FOR SEQ ID NO:49:

( i ) SEQUENCE CHARACTERISTICS:
  ( A ) LENGTH: 27 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:49:

CGACATATTA TGTGCCAACA ATGACGC 27

( 2 ) INFORMATION FOR SEQ ID NO:50:

( i ) SEQUENCE CHARACTERISTICS:
    ( A ) LENGTH: 27 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:50:

ATGTCAGCAG CGTGCGCAGA ACAGCGT 27

( 2 ) INFORMATION FOR SEQ ID NO:51:

( i ) SEQUENCE CHARACTERISTICS:
    ( A ) LENGTH: 50 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:51:

CAGCGTGAGT TATGCTCACG CCGCGGAGAC ATGTCCTGCA CGATTACGCG 50

( 2 ) INFORMATION FOR SEQ ID NO:52:

( i ) SEQUENCE CHARACTERISTICS:
    ( A ) LENGTH: 27 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:52:

ATGAGCCAGC GTTGCTTAAA ATCACGC 27

( 2 ) INFORMATION FOR SEQ ID NO:53:

( i ) SEQUENCE CHARACTERISTICS:
    ( A ) LENGTH: 27 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:53:

ATGTCCGCGA CGTGCAGCGC TGGATCT 27

( 2 ) INFORMATION FOR SEQ ID NO:54:

( i ) SEQUENCE CHARACTERISTICS:
    ( A ) LENGTH: 57 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:54:

AGCCAGCGTG AGTTAAAATC ACGCCGCGGA GACATGTTCG CGACGATTAC GCGTGGA    57

( 2 ) INFORMATION FOR SEQ ID NO:55:

( i ) SEQUENCE CHARACTERISTICS:
        ( A ) LENGTH: 45 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:55:

CGTGAGTTAA AANNSNNSCG CGGAGACNNS NNSGCGACGA TTACG    45

( 2 ) INFORMATION FOR SEQ ID NO:56:

( i ) SEQUENCE CHARACTERISTICS:
        ( A ) LENGTH: 45 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:56:

CGTGAGTTAA AANNSCGCCG CGGAGACATG NNSGCGACGA TTACG    45

( 2 ) INFORMATION FOR SEQ ID NO:57:

( i ) SEQUENCE CHARACTERISTICS:
        ( A ) LENGTH: 45 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:57:

CGTGAGTTAA AATCANNSCG CGGAGACNNS TCCGCGACGA TTACG    45

( 2 ) INFORMATION FOR SEQ ID NO:58:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:58:

AGCCAGCGTG AGNNSNNSTC ACGCCGCGGA GACATGTCCN NSNNSATTAC GCGTGGA    57